(12) United States Patent
Fonash et al.

(10) Patent No.: US 6,399,177 B1
(45) Date of Patent: Jun. 4, 2002

(54) DEPOSITED THIN FILM VOID-COLUMN NETWORK MATERIALS

(75) Inventors: Stephen J. Fonash; Ali Kaan Kalkan; Sanghoon Bae, all of State College, PA (US)

(73) Assignee: The Penn State Research Foundation, University Park, PA (US)

( * ) Notice: Subject to any disclaimer, the term of this patent is extended or adjusted under 35 U.S.C. 154(b) by 58 days.

(21) Appl. No.: 09/580,105

(22) Filed: May 30, 2000

Related U.S. Application Data

(60) Provisional application No. 60/137,385, filed on Jun. 3, 1999, provisional application No. 60/139,608, filed on Jun. 17, 1999, and provisional application No. 60/161,848, filed on Oct. 27, 1999.

(51) Int. Cl.$^7$ ................................................ B32B 7/00
(52) U.S. Cl. ........................................ 428/119; 428/469
(58) Field of Search ................................. 428/119, 469

(56) References Cited

U.S. PATENT DOCUMENTS

| | | | |
|---|---|---|---|
| 5,093,149 A | | 3/1992 | Doehler et al. ................ 427/38 |
| 5,358,600 A | | 10/1994 | Canham et al. ............. 156/644 |
| 5,627,382 A | | 5/1997 | Canham et al. ................ 257/3 |
| 5,866,204 A | * | 2/1999 | Robbie et al. ............. 427/256 |
| 5,882,496 A | | 3/1999 | Northrup et al. ........... 204/601 |
| 6,086,679 A | | 7/2000 | Lee et al. .................... 118/724 |
| 6,279,504 B1 | * | 8/2001 | Takaki et al. ............... 118/723 |

OTHER PUBLICATIONS

Messier et al., Evolution of microstructure in amorphous hydrogenated silicon, J. Appl. Phys. 53(9), Sep. 1982, pp. 6220–6225.

Bae et al., Characteristics of amorphous and polycrystalline silicon films deposited at 120°C by electron cyclotron resonance plasma–enhanced chemical vapor deposition, J. Vac. Sci. Technol. A 16(3), May/Jun. 1998, pp. 1912–1916.

Hong et al., Structural and electrical characterization of microcrystalline silicon films prepared by a layer–by–layer technique with a plasm–enhanced chemical–vapor deposition system, J. Appl. Phys. 87(4) Feb. 15, 2000, pp. 1676–1680.

Cullis et al., The structural luminescence properties of porous silicon, Appl. Phys. 82 (3), Aug. 1, 1997, pp. 909–965.

Canham, Silicon quantum wire array fabrication by electrochemical and chemical dissolution of wafers, Appl. Phys. Lett. 57 (10), Sep. 3, 1990, pp. 1046–1048.

(List continued on next page.)

Primary Examiner—Deborah Jones
Assistant Examiner—Gwendolyn Blackwell-Rudasill
(74) Attorney, Agent, or Firm—Ohlandt, Greeley, Ruggiero & Perle, L.L.P.

(57) ABSTRACT

A novel porous film is disclosed comprising a network of silicon columns in a continuous void which may be fabricated using high density plasma deposition at low temperatures, i.e., less than about 250° C. This silicon film is a two-dimensional nano-sized array of rodlike columns. This void-column morphology can be controlled with deposition conditions and the porosity can be varied up to 90%. The simultaneous use of low temperature deposition and etching in the plasma approach utilized, allows for the unique opportunity of obtaining columnar structure, a continuous void, and polycrystalline column composition at the same time. Unique devices may be fabricated using this porous continuous film by plasma deposition of this film on a glass, metal foil, insulator or plastic substrates.

53 Claims, 15 Drawing Sheets

OTHER PUBLICATIONS

Messier et al., Revised structure zone model for thin film physical structure, J. Vac. Sci. Technol. A 2 (2), Apr.–Jun. 1984, pp. 500–503.

Gu et al., Silicon nanowires grown on iron–patterned silicon substrates, Appl. Phys. Lett. 76(21), May 22, 2000, pp. 3020–3021.

Kalkan et al., Nanocrystalline Si thin films with arrayed void–column network deposited by high density plasma, J. Appl. Phys. (88)1, Jul. 1, 2000, pp. 555–561.

Messier et al., Black a–Si solar selective absorber surfaces, J. Appl. Phys. 51(3), Mar. 1980, pp. 1611–1614.

* cited by examiner 6 mTorr 8 mTorr 10 mTorr

DEPOSITED THIN FILM VOID-COLUMN NETWORK MATERIALS

This application claims the benefit of U.S. Provisional Application No. 60/137,385 filed Jun. 3, 1999, U.S. Provisional Application No. 60/139,608 filed Jun. 17, 1999, and U.S. Provisional Application No. 60/161,848 filed Oct. 27, 1999, the contents of which are hereby incorporated by reference into this application.

BACKGROUND OF THE INVENTION

1. Filed of the Invention

The present invention relates to the production of a high porosity semiconductor thin film via a plasma-enhanced chemical-vapor deposition system. More specifically, the present invention relates to a unique high density plasma approach which uses simultaneous plasma deposition and etching to obtain high porosity semiconductor thin film.

2. Description of Related Art

There is a great deal of interest in porous silicon structures. The reasons for this are two-fold. First, these porous films can be used in a variety of applications including MEMS (microelectro-mechanical devices), interconnect dielectic, micro-sensor, cell and molecule immobilization, and micro-fluidic applications. Secondly, the material is very compatible with Si microelectronics. There are various approaches to producing porous silicon materials. The technique attracting the most attention today for the fabrication of porous silicon is based on the use of wet chemical solutions and the electrochemical technique of anodization (R. C. Anderson, R. C. Muller, and C. W. Tobias, Journal of Microelectromechanical System, vol. 3, (1994), 10). Heretofore, this technique has yielded the best level of porosity among known approaches. The starting material for this wet etched material is either conventional silicon wafers or thin film Si produced by some deposition process such as low pressure chemical vapor deposition (LPCVD) or plasma enhanced chemical vapor deposition (PECVD). In the electrochemical wet etching process the sample is exposed to a wet solution and a current is passed through a contact to the etching sample, through the etching sample, through the solution (e.g., a mixture of hydrofluoric acid, water and ethanol), and through an electrode contacting the solution (the cathode; e.g., platinum). This current causes the "pitting" or etching of the Si producing a porous network structure.

In the electrochemical (anodic) etching process the structure (e.g., pore size and spacing) and the porous-Si layer thickness are controllable by the resistivity of the silicon itself (magnitude and type), current density, applied potential, electrolyte composition, application of light, temperature, and exposure time. For sufficiently long exposures and for sufficiently thick starting material, this electrochemical etching process can be continued to the point where nanoscale structure (i.e., features of the order of nanometers) is obtained. The silicon features are a continuous single crystal when the sample is etched from a single crystal wafer or large grain polycrystalline silicon when the sample is etched from a deposited film. All these conventional (electrochemically etched) porous silicon materials are distinguished by (1) being the result of a wet, electrochemical etching process, (2) requiring a contact on the sample during this wet etching, (3) having generally disconnected pore regions which can be connected after extensive etching, and (4) being the result of a sequential processing first necessitating formation of the silicon and then necessitating subsequent wet etching.

Intense research activity in porous semiconductors has been even further stimulated over the last decade by the discovery of room temperature visible light emission from electrochemically prepared porous Si in 1990 by Canham (L. T. Canham, Appl. Phys. Lett. 57, 1046 (1990)), Soon after Canham's discovery, further intriguing properties of porous semiconductor materials were also realized, such as gas sensitivity, bio-compatibility and ease of micromachining, etc. (I. Schecter et al., Anal. Chem. 67, 3727 (1995); J. Wei et al. Nature 399, 243 (1999); L. T. Canham et al., Thin Sold Films, 297, 304 (1997); P. Steiner et al., Thin Solid Films 255, 52 (1995)). All demonstrated applications to-date have been based on porous silicon material produced by electrochemically etching a wafer or deposited film of silicon.

The approach to porous silicon in the present invention is to use deposition to grow as-deposited porous films; specifically the porous silicon is a deposited columnar material whose pores are the voids between the columns and clusters of columns. In the present invention, pores (void) regions are reasonably uniform through the thickness of the film and across the film. The present process is unique because it is performed at low temperature, the present inventors have demonstrated that the present invention can be used to control void size and void fraction, the void-column network morphology does not vary over thicknesses of interest, the columns can be polycrystalline material, and a plasma approach can be used to control the interaction between deposition and etching during growth. The present process yields high porosity (of up to approximately 90%), controlled pore size material without any back contacts and anodization-based wet processing. Unlike other deposition processes, the present process is based on high-density plasma deposition-etching interaction and is, therefore, able to give a high degree of controllable porosity (up to 90%), a morphology that does not vary with thickness, and doped or un-doped polycrystalline columns. Also unique to the present invention is its ability to fabricate this porous silicon on various types of substrates including glass, metal foils, insulators, plastic, and semiconductor-containing materials.

The high density plasma (HDP) deposition tool used in this demonstration was an electron cyclotron resonance plasma machine. In particular, our porous silicon was demonstrated by use of a high density plasma tool (e.g., Electron Cyclotron Resonance Plasma Enhanced Chemical Vapor Deposition (ECR-PECVD) tool (PlasmaTherm SLR-770)) using hydrogen diluted silane ($H_2$:$SiH_4$) as the precursor gas at substrate deposition temperatures less than or equal to about 250° C. This tool plays off silicon etching and deposition to create a two-dimensional silicon array and analysis has demonstrated that silicon column size is controllable, the spacing between columns is controllable, and morphology does not vary with thickness. Unlike other deposited columnar silicon materials, the column spacing can be maintained as the film grows in thickness and column phase composition can be controllably varied from polycrystalline to amorphous. The resulting void-column network structure is nanoscale in feature size and fully developed after a film thickness in the range of 10–20 nm is established. This enables the direct deposition of high porosity crystalline or amorphous silicon on any substrate and at any thickness greater than about 10 nm, and preferably between 10–20 nm. The porous semiconductor films produced by the present invention may be converted to insulators or metallic compounds through in situ or ex situ processing.

The prior art contains two approaches to porous silicon: (1) wet electrochemical etching of deposited silicon or of silicon wafers to produce a porous silicon with a "coral-like" morphology of polycrystalline or single-crystal silicon "fingers" or (2) deposition of silicon to produce a porous material consisting of tapered amorphous silicon rods with a morphology that varies with thickness. The former material has the advantage of a very controllable morphology and porosity and is the subject of a great deal of research and development activity. However, it requires wet chemical etching for its formation. The latter material suffers from only being available in the amorphous phase and of having a morphology that varies with thickness and a porosity that requires subsequent wet etching for control. The porous silicon of this invention requires no wet processing. It has a fully controllable morphology and porosity and can be in the polycrystalline or amorphous phase as desired.

This invention describes porous material deposition at low temperatures. These materials are particularly suitable for deposition on glass or plastic or other substrates requiring low processing temperatures such as substrates containing previously formed sensor, electronic or opto-electronic devices and circuits. Due to the wide, demonstrated porosity range possible for the materials of this invention, they can be used for a number of applications including sensing, airgaps (optical mixing, microfluidics, molecular sorting, low dielectric constant structures, etc.), fixing and electrically contacting molecules and cells, and mass desorption applications. The invention is demonstrated using deposited porous silicon.

SUMMARY OF THE INVENTION

The present invention provides a deposited porous film comprising a plurality of perturbations extending therefrom into a void having a porosity of up to about 90%. The plurality of perturbations are disposed substantially perpendicular to a substrate, or in the alternative, to a base layer. The plurality of perturbations are rod-like shaped columns and are semiconducting, and may be polycrystalline, such as a silicon material. The porosity is the result of a continuous void. The perturbations have a height adjustable by the film thickness and are of a diameter from about 1 nm to about 50 nm. More specifically, the columns have a diameter of about 3 nm to about 7 nm. Further, the perturbations are found in clusters having a diameter between about 50 to 500 nm or more.

The present invention also provides a composite structure which comprises a substrate; and a porous film comprising a plurality of perturbations extending therefrom into a void having a porosity of up to 90%, wherein the porous film is disposed on the substrate. The composite structure may further comprise a coating layer, such that the porous film is disposed on the coating layer. The coating layer is at least one of the following materials: insulators such as organic insulators, silicon nitride, and silicon oxide; or at least one of the following active materials: piezoelectrics, ferroelectrics, metals, and semiconductors. The composite structure may further comprise a capping layer, such that the porous film is disposed between the capping layer and the substrate, where the substrate may be coated. The capping layer is at least one of the following materials: insulators such as organic insulators, silicon nitride, and silicon oxide; or at least one of the following active materials: piezoelectrics, ferroelectrics, metals, and semiconductors. The porous film has a thickness greater than about 10 nm, and wherein the film may be varied from polycrystalline to amorphous. This deposited porous film is structured in a two-dimensional periodic array of rod-like perturbations. The porous films can be converted; e.g., oxidized to $SiO_2$, reacted with metals to form silicides or nitrided to $Si_3N_4$. The film may also be doped or not doped. The substrate of the composite structure is selected from glass, metals including foils, insulators, plastics, and semiconductor-containing material. The substrate may optionally be coated with an atomic motion barrier, thermal barrier, electrically insulating, or stress-controlling film. An example film is a silicon nitride barrier layer, wherein the thickness of this silicon nitride barrier layer can vary from hundreds of Angstroms or less, to about 5,000 nm. The film may be varied during deposition and throughout the film thickness.

The present invention further provides a method of forming a composite structure comprising a substrate and a porous film. This method comprises the step of depositing a porous film on a substrate via high density plasma deposition. The porous film of this method comprises a plurality of perturbations extending therefrom into a void having a porosity of up to about 90%. The method may further comprise the step of etching the porous film, where the deposition and etching steps preferably occur simultaneously. The etching can be conducted by the presence of corrosive agents in the plasma such as hydrogen, chlorine, fluorine, HCl, HF and their derivative radicals. The above-mentioned high density plasma deposition is conducted in the presence of at least one precursor gas, selected from hydrogen and silicon-containing gas. More specifically, the silicon-containing gas is silane ($SiH_4$ gas). The deposition step is conducted at a temperature of about 250° C. or less, and in the presence of a magnetic field at the substrate region in the range between about +800 to −600 Gauss, and in an excitation of microwave power in the range between about 100 Watts to 1200 Watts. The deposition step is also conducted with no impressed voltage between the plasma and substrate. An additional step in the method can be removing the porous layer in the selected regions of porous film by etching, thereby creating an airgap, release, or isolation structure.

More specifically, the present invention provides a method wherein this method is comprised of the steps of preparing a substrate; conditioning the deposition tool surfaces; employing a plasma deposition tool to create ions, radicals, and other excited species; introducing power into a plasma chamber; feeding precursor gases into the plasma deposition tool to ignite the plasma; using controls to further adjust deposition kinetics; and depositing films on a substrate via plasma deposition.

The substrate may further be coated prior to porous film deposition depending on the type of substrate implemented. The substrate is coated using a material selected from those useful for functions such as electrical isolation, planarizing, atomic motion barrier, stress adjustment, and thermal coupling. The substrate may be exposed to surface texturing such as liquid chemical etching or plasma chemical etching.

The plasma deposition tool used in the above method is a high density plasma deposition tool. A specific high density plasma deposition tool for the method is an electron cyclotron resonance tool.

The porosity is controllable with substrate treatments such as coating, plasma power, substrate-region magnetic field, gas composition, deposition temperature, plasma substrate bias, chamber conditioning, process pressure, deposition gases and flow rates. The energy of the plasma species impacting the depositing/etching film is important and must be kept low. This control is assured by a high density plasma system; e.g., in an ECR tool the kinetic energy of the impacting species is expected to be <45 eV.

The present invention also allows for controlling the column phase. For example, at high deposition pressures (e.g., 20 mTorr) the columns will become amorphous instead of polycrystalline in the case of silicon.

Further, the present invention provides for a method of producing a porous film, comprising the steps of preparing the substrates with steps such as barrier coatings; conditioning the chamber; employing a high density plasma deposition tool to create ions, radicals, and other excited species; introducing power into a plasma chamber; feeding precursor gases such as $H_2$ gas into the plasma chamber to ignite the plasma; and $SiH_4$ gas into the deposition chamber; maintaining a temperature for substrate deposition of less than about 250° C.; using controls such as substrate-region magnetic field to further adjust deposition kinetics; and depositing films on a substrate.

The microwave power introduced into the ECR plasma chamber is from between about 100 Watts to 1200 Watts, preferably between about 340 Watts to 640 Watts. The microwave power used had a frequency of 2.45 GHz.

The $H_2$ flow rate for the present invention is between about 1 sccm to 500 sccm, preferably between about 10 to 100 sccm. The $SiH_4$ flow rate for the present invention is between about 1 sccm to 300 sccm, preferably between about 2 to 10 sccm.

More specifically, the present invention encompasses a method for producing the above-described film, comprising the steps of: employing a high density plasma deposition tool with a precursor gas, such as hydrogen diluted silane ($H_2$:$SiH_4$); introducing microwave power between about 100 Watts to 1200 Watts into a ECR plasma chamber through a waveguide and a fused quartz window minimizing reflected power by adjusting a tuner; setting up a static magnetic flux density in the vicinity of the substrate of +800 to about −600 Gauss using a DC electromagnet; feeding $H_2$ gas at about 1 sccm to 500 sccm through a gas dispersal ring in the ECR plasma chamber; injecting $SiH_4$ gas at about 1 sccm to 300 sccm through a gas distribution ring about 1.3 cm above the substrate into the deposition chamber; maintaining a temperature for substrate deposition of less than 250° C.; and depositing films on a substrate.

The present invention may be used in forming sensors, desorption spectroscopy structures, gas detectors, and airgap (void) structures for plasma display applications, for dielectric applications, for monitoring lateral resistivity and for tube, sorting, and chromatography applications, and for optical structures such as in opto-electronic devices and solar cells for optical impedance applications. These uses typically comprise a composite structure having a substrate; and a porous continuous film comprising polycrystalline or amorphous silicon having a porosity of up to 90% wherein the porous continuous film is disposed on the substrate.

BRIEF DESCRIPTION OF THE DRAWINGS

FIG. 12b is a top planar view of an isolation region created from the materials of FIG. 12a; and FIG. 12c is a cross-sectional view along line C—C of FIG. 12a.

DETAILED DESCRIPTION OF THE INVENTION

Figure 1:
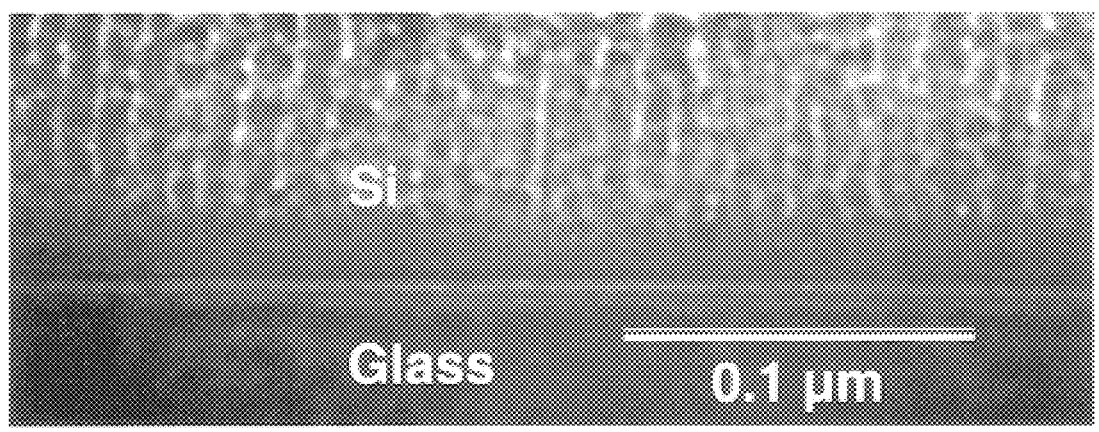
FIG. 1 is a cross sectional TEM micrograph of a void-columnar network silicon thin film on glass.

The present invention describes a unique high density plasma approach which uses simultaneous plasma deposition and etching to obtain high porosity crystalline or amorphous semiconductor thin films. All dry processing is used in the film formation and no wet processing need be involved. With proper conditioning of the processing chamber, proper preparation of the substrate, and proper selection of the deposition parameters, these films always have a controllable and adjustable void-column network morphology with interconnected voids (pores) and untapered columns normal to the substrate. Unlike conventional porous silicon which is produced by wet etching, this interconnected continuous void network occurs for any film thickness greater than about 10 to 20 nm. Unlike conventional porous silicon, the present films may or may not be doped. Also, unlike conventional porous silicon, the continuous void-column network materials of the present invention can be produced on a variety of substrates such as glass, metal foils, and plastics, as well as the more conventional substrates such as silicon wafers. As an example, silicon and an ECR high density plasma (HDP) tool were used in a demonstration. This experiment also established visible luminescence, gas sensitivity, airgap structure formation, desorption mass spectroscopy, etc. The present invention's distinct continuous void (pore) arrangement, oriented columns and uniform nanostructure, low temperature processing, and unique process exploit the advantages of plasma deposition technology offering many new possibilities unhindered by the need for wet processing, wet etching, and the relatively thick starting material needed in the conventional approach to obtain small feature sizes by wet etching. This invention also has a number of technological and economical advantages compared to the conventional porous silicon fabrication techniques.

Unlike other textured deposited and columnar deposited silicon films, the present process is not a sputtering deposition technique with its possibility of sputter damage. It is a plasma etching/deposition technique producing films that can be deposited at very low temperatures, can have amorphous or polycrystalline columns, have high density levels of porosity (up to 90%), can have doped or un-doped columns, have a morphology that does not vary with thickness, and are very controllable allowing void (i.e., pore) size to be tailored to an application. Since the process temperatures during the film depositions are very low (i.e., room temperature to approximately 250° C.), the technique places no restriction on substrates.

A high density plasma source was used to produce the present continuous void/perpendicular untapered column morphology. In particular in the experiment, an ECR (Electron Cyclotron Resonance) high density plasma (HDP) PECVD system was used. In the HDP approach towards high porosity films, an Electron Cyclotron Resonance Plasma Enhanced Chemical Vapor Deposition (ECR-PECVD) tool was employed (PlasmaTherm SLR-770) with hydrogen diluted silane ($H_2$:$SiH_4$) as the precursor gas at substrate deposition temperatures less than 250° C. The deposition apparatus consists of two coaxially connected plasma chambers, i.e. an ECR chamber and a deposition chamber, which are 14.9 and 35.6 cm in diameter and 13.3 and 29.2 cm in height, respectively. To ignite the plasma, microwave power with an excitation frequency of 2.45 GHz is introduced into the ECR plasma chamber through a rectangular waveguide and a fused quartz window. Reflected microwave power is forwarded by a directional coupler to a dummy load and a three-stub tuner is used to minimize the reflected power. The substrate bias, which can be independently controlled with 13.56 MHz RF power supply to independently adjust substrate bombardment, was off to reduce bombardment energy. To meet the electron cyclotron resonance condition, a DC-electromagnet located coaxially around the ECR chamber generated an upper magnetic field with a static magnetic flux density of 875 gauss (G) within the ECR chamber. $H_2$ is introduced into the ECR chamber through a gas distribution ring close to the quartz window. $SiH_4$ is injected into the deposition chamber through a gas inlet ring about 1.3 cm above the location of the substrate (27.9 cm below the ECR chamber). Hydrogen gas and silane were used in the experiments although other hydrogen and silicon-bearing precursors, in the case of void-column network Si films, could be employed. The $H_2$ (99.999%) was fed through a gas dispersal ring in ECR chamber to ignite the ECR plasmas while $SiH_4$ (99.999%) was introduced through a gas distribution ring around the substrate-holding fixture. Hydrogen was fed into the ECR chamber to start the ECR plasmas for the silicon films in this study. A secondary DC-electromagnet is placed just below the substrate level to establish an adjustable magnetic flux density which can vary from about +800 to −600 Gauss. This flux exists around the substrate. The vacuum chamber holding the substrates was pumped by a turbomolecular pump and the base pressure was lower than $4 \times 10^{-7}$ torr, such at a base vacuum pressure of $2 \times 10^{-7}$ torr. Table 1 lists the range of plasma deposition parameters explored. The films were deposited on Corning 1737 glass substrates coated with an 80 nm thick silicon nitride barrier layer (unless otherwise stated). The film thickness was measured with a Tencor-500 profilometer. The nanostructure was studied with cross sectional TEM (Hitachi HF-2000 cold filed emission) and AFM (Atomic Force Microscopy) (Digital Instruments Multimode AFM system with NanoScope IIIa Controller). The AFM was used in the TappingMode™ with an Olympus cantilever and etched silicon tetrahedral probe with a tip angle of ~35° C. and radius of 5–10 nm. An X-ray diffractometer (Phillips X'pert) with a glancing incidence optics was employed to investigate the crystallinity. UV reflectance of the films were obtained with a Perkin Elmer Lambda 9 spectrometer to assess the level of porosity. Photoluminescence was measured with an ISA U-1000 Raman spectrometer using a 488 nm Ar-laser excitation of 5 mW.

The temperature of the substrate-holding fixture was controlled by a heater and chilled water (T=16° C.). Helium substrate back-side cooling was also employed to control the deposition temperature during plasma operation.

When electrical contacts were used with these void-column network films, these were defined on the film surface in parallel stripe (19 mm in length) configuration (with 0.4 mm spacing) to monitor the conductivity variation in response to various gas ambients. In the specific case of relative humidity (RH) measurements, the samples were situated in a glass tube on a Teflon stage with two Au probes in contact with the stripe electrodes. The RH inside the glass tube was gradually ramped from about 2% to about 97% in the glass tube at 20° C. by flowing $N_2$ as the humidity carrier through a heated bubbler and then into the tube. A capacitive type sensor was used as reference to measure RH (TI-A from TOPLAS CO., Japan) with an HP-4284A LCR-meter, while the enhancement in current for a fixed voltage was traced for the void-column structures with an HP-4140B pA-meter/DC voltage source.

The observed morphologies for the conventional electrochemically prepared porous Si are classified as "microporous" (pore width less than 20 Å), "mesoporous" (pore width 20–500 Å) and "macroporous" (pore width greater than 500 Å) corresponding to a variation in the characteristic pore size of from nanometers to microns, respectively (A. G. Cullis, L. T. Canham, P. D. J. Calcott, J. Appl. Phys. 82, 909, (1997)). Whether a "conventional" porous silicon is microporous, mesoporous, or macroporous depends on parameters such as starting material thickness, doping type and level, crystal orientation, time of wet etching, etc. According to this "pore size" classification the present films are closest to the "conventional" porous silicon termed microporous silicon, which is typically obtained from $p^+$ or $p^-$ silicon. When $p^+$silicon is subjected to anodization, long pores along the direction perpendicular to the silicon surface form at widths in a range around 10 nm. However, the morphology shows a considerable degree of randomness as the pores themselves are heavily branched and exhibit a very characteristic "fir tree" configuration (M. I. J. Beale, J. D. Benjamin, M. J. Uren, N. G. Chew, A. G. Cullis, J. Cryst. Growth 73, 622 (1985)). In the case of microporous anodized $p^-$ silicon, the material shows an irregular coral-like microstructure which is composed of highly interconnected micropores in the size range less than 2 nm (Beale et al.).

Figure 2:
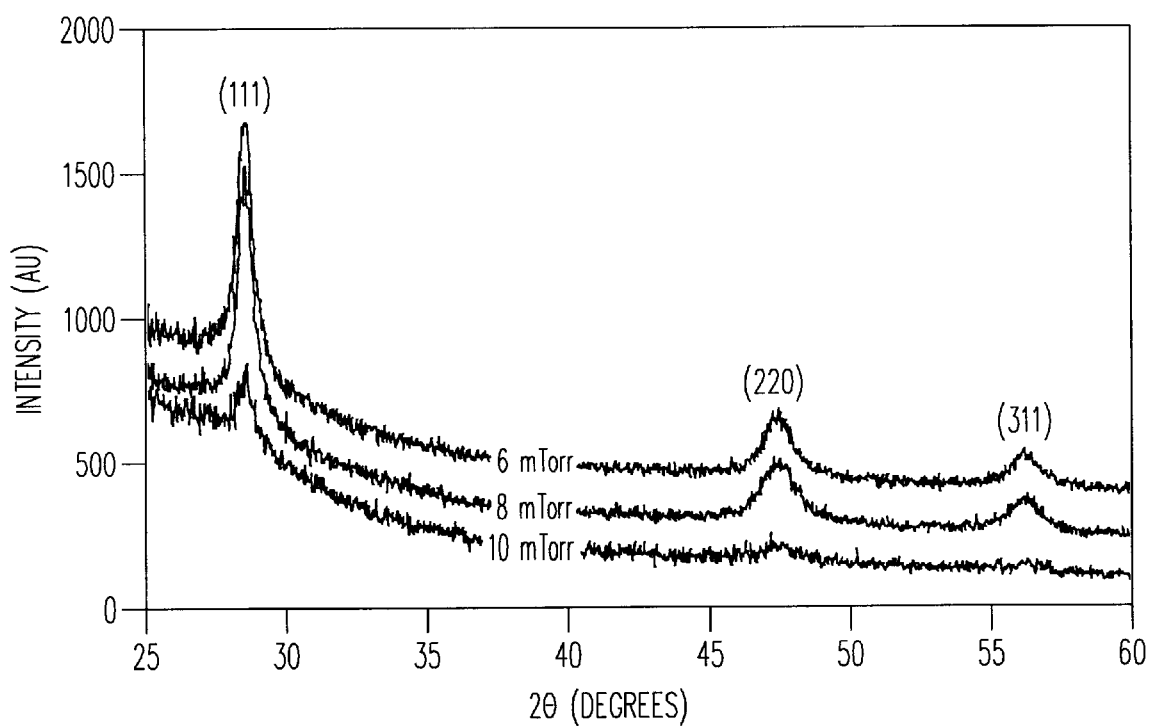
FIG. 2 is a graph of XRD patterns of the void-columnar films deposited at 100° C. and various pressures of 6, 8 and 10 mTorr.

The morphology of the present films is very different from these firtree or coral-like structures. The nanostructure of the Si films, deposited by the high density plasma tool approach, consists of an array of rodlike columns normal to the substrate surface and situated in a continuous void matrix. FIG. 1 shows the TEM view of the nanostructure of a film deposited at a temperature of 120° C., process pressure of 7.8 mTorr and microwave power of 500 W. These columns of FIG. 1 are in clusters (not seen at this very high magnification). A careful examination of the columns show that in the parameter range where they are crystalline, the columns are made up of granular crystalline grains whose size is that of the column diameter. In this case, the grains constituting a column are situated on top of one another. Undulations in between the columns (i.e., changes in the size) are seen to occur due to statistical variations in grain size. However, at a larger scale, (for example, averaged across the film) the column spacing and size and void spacing between column clusters are generally uniform. The voids are interconnected even for lower porosities resulting in a continuous void network throughout the film. Therefore, compared with the observed morphologies of the electrochemically etched porous silicon these deposited void-column network films show a distinct nanostructure and, most importantly, a higher degree of uniformity. The unique morphology of the films occurs for all films of thickness of about approximately 10 nm or more. The XRD pattern in FIG. 2 identifies the three films deposited for 35 minutes at 100° C. and various powers 6, 8, and 10 mTorr to be crystalline.

The structure zone model (SZM) introduced by Movchan and Demchishin (B. A. Movchan and A. V. Demchishin, Fiz. Met. Metalloved. 28, 653 (1969)) and developed by Thornton (J. A. Thornton, J. Vac. Sci. Technol. 11, 666 (1974), J. Vac. Sci. Technol. 12, 830 (1975) and Messier (R. Messier, A. P. Giri, R. A. Roy, J. Vac. Sci. Technol. A2, 500 (1984)) was established to discuss the morphology expected for sputter deposited films. Although our films are deposited/etched using a high density plasma approach, if one used the SZM, the structure of these porous-silicon films would be expected to fall into what is termed zone 1 morphology.

In this zone 1, the films consist of tapered columns (typically tens of nm in diameter) separated by voids (typically a few nm across). Because of the tapered columns, this zone 1 structure evolves with thickness. Zone 1 structure is expected for the present films because the deposition temperature used is very low compared to the melting temperature of the deposited material and the diffusion length of the molecules or atoms on the deposition surface is less than the average distance between the physisorption sites. In addition, the kinetic energy of the impinging ions is less than or about the sputtering threshold (of the silicon film). Therefore, for these reasons the depositing species would be expected to become immobilized where they land. This is known as "ballistic" deposition. At these conditions, two factors are responsible for the generation of voids; i.e., statistical roughening and self-shadowing. However, these mechanisms lead to randomly shaped voids and tapered ("cauliflower-shaped") columns, respectively. These conditions lead to a morphology that evolves with film thickness. The present films are not sputter deposited. They are produced by plasma deposition/etching. They have voids and columns that are very different from this expected result. In addition, the control of the void sizes, degree of porosity, and columns of the present films are very different from that expected. The uniqueness of this invention is in its ability to give controlled porosity, columns, and doped or un-doped polycrystalline or amorphous material in a void-column network structure that does not evolve with thickness. Usually it is not possible to have all of these features in a one-step process. Put succinctly, the uniqueness of this invention lies in its ability to take advantage of low surface diffusion for the creation of voids and its ability to take advantage of high density plasma reactions, which promote etching and controllable crystallinity despite this low surface mobility. On the other hand, with a conventional PECVD approach in the absence of high density plasma chemistry, the low surface mobility will limit the structure to amorphous. Therefore, obtaining at the same time a controlled high void fraction, controlled crystallinity, and a morphology that does not evolve with thickness is expected to be out of the question.

The void networks and their evolution with film thickness in amorphous-silicon films deposited by RF-sputtering has been extensively studied by Messier and co-workers. (R. Messier and R. C. Ross, J. Appl. Phys. 53, 6220, (1982)). The present films can be controlled to be polycrystalline silicon and can be up to approximately 90% porous. The Messier et al. work dealt with amorphous silicon and did not show how to get the degree of porosity that the present technique can yield, unless post deposition, wet etching was carried out (R. Messier, S. V. Krishnaswamy, L. R. Gilbert, P. Swab, J. Appl. Phys. 51, 1611 (1980)). In the high density plasma, very low processing-temperature approach used here, deposition and hydrogen radical etching (resulting in an etching-deposition process) is presumed to play an important role in the formation of the nanostructure. A possible mechanism is that, in the presence of high density of hydrogen radicals, once the crystalline nuclei form, the bonding at these crystalline nuclei sites is stronger and withstands hydrogen radical etching while the bonding elsewhere is weaker and can be etched by the hydrogen radicals. As a result, the growth follows crystalline nuclei leading to formation of regularly shaped, aligned protruding columns of the void-column network films. The reason why lateral growth is not allowed to form columns increasing in diameter with increasing film thickness (i.e., cone-shaped or cauliflower-shaped columns) in the process has not been understood yet. This may be due to severe hydrogen etching promoting very directional growth. Before the columnar growth initiates, a void free amorphous-like layer forms at the substrate interface. From FIG. 1 the thickness of this transition region is measured to be about 20 nm for this sample. The void-column network of the porous films is then coated on top of this transition layer.

The special attributes of the deposited void-column network-type of porous silicon (i.e., a morphology that does not evolve with thickness having non-tapered columns oriented perpendicularly to the transition layer and penetrating through a continuous void) are controlled by a number of factors. These include the (a) voltage between plasma and substrate, (b) substrate temperature, (c) plasma power and process pressure, (d) magnetic field in the vicinity of the substrate, (e) deposition gases and flow rates, (f) chamber conditioning, and (g) substrate surface. The influence of a number of these factors is not what would be expected.

The range of some of the key parameters used in this study is outlined in Table 1 below.

TABLE 1

(Process conditions)

| Parameters | Range |
| --- | --- |
| $H_2$ flow (sccm) | 1–500 |
| $SiH_4$ flow (sccm) | 1–300 |
| Microwave (2.45 GHz) power (Watts) | 100–1200 |
| RF (13.56 MHZ) substrate bias (Watts) | 0–100 |
| Process pressure (mtorr) | 2–15 |
| Deposition temperature (° C.) | 20–250 |
| Magnetic field intensity in the vicinity of the substrate (Gauss) | +800 to −600 (+ sign: same direction as the top magnet − sign: opposite direction as top magnet) |

These variants are discussed in detail below.

Voltage Between Plasma and Substrate (RF Substrate Bias)

The accelerating potential (i.e. substrate bias) between the plasma and the substrate can be independently controlled in high density plasma (HDP) tools. This factor is independently available and variable in HDP deposition machines. That is, in this class of tools, this voltage may be adjusted independently of the plasma power, which is not the case in conventional RF or DC plasma deposition systems. In the electron cyclotron resonance (ECR) high density plasma tool used to demonstrate the HDP deposited porous films, this voltage is controlled, independent of the plasma power, by applying an RF bias between the plasma and substrate.

As presented in an article discussing thin film silicon deposition (S. Bae, A. K. Kalkan, S. Cheng, and S. J. Fonash, J. Vac. Sci. & Tech. A16, p. 1912 (1998)) it was shown that the presence of an RF bias between the plasma and substrate destroyed the columnar morphology and allowed one to obtain a continuous film with no pore structure. In fact, the purpose of the JVST article was to teach how to avoid the porous-type film; i.e., purpose of that article was to show how to get rid of the columnar morphology possible with the films. At the time of that article, it was not known that the columns of the films were not tapered, did not display the usual cauliflower shape seen in previous columnar silicon films, and had a fully controllable porosity. It was also not known that the present void structure was a unique and continuous void. At the time of the article, the columnar films were thought have typical Zone I structure with a morphology that evolved with thickness and columns which would be tapered. Hence, at the time of the JVST article, the objective of the publication was to teach how to avoid formation of the columnar version of the deposited silicon film. As the JVST article teaches, the columnar morphology can be avoided with the application of the RF bias between the plasma and substrate and the effectiveness of this RF bias approach is demonstrated in this article. The avoidance of Zone I columnar formation with increased energy (increased RF substrate bias) of species arriving at the growing film surface is the behavior that would be expected from the structure zone model. The depositing species would have more energy with increasing RF substrate bias and the resulting increase in surface mobility would lead to a pore-free, column-free homogeneous film. This is the behavior expected and discussed in the JVST article.

For creation of the present thin film void- deposited column network materials, it was discovered that the best film morphology (non-tapered, non-cauliflowered columns) is obtained for the lowest value of the voltage between the plasma and substrate (i.e., zero RF substrate bias). In the present ECR system this is attained for an RF bias voltage of zero for any plasma power level.

Substrate (Deposition) Temperature

Increasing the substrate temperature during deposition also increases surface mobility. Hence, as is predicted from the structural zone model, porosity decreases in the films with increasing substrate temperature. However, what is not expected and what we did not discuss in the JVST article, is that the columns continue to be uniform (i.e., untapered) and aligned with no tendency toward a cauliflower-type growth over the temperature range we explored ($50°$ C.$<T<250°$ C.). The film does not display morphology evolution with film thickness. The point to be noted is that temperature, over the range defined, has been found to be a tool for adjusting porosity, as one would expect, but, surprisingly, this can be accomplished without losing the oriented, untapered uniform columns protruding through the continuous void (pore) network. This point is unexpected and not discussed previously in the art.

Plasma (Microwave) Power/Process Pressure

Using the structural zone model one would expect increasing plasma microwave power would lead to more energetic surface species and therefore to less porosity. What was discovered happens, however, is that if all factors except plasma power and process pressure are fixed, then porosity does decrease with power but surprisingly the oriented, untapered, uniform columns protruding through the continuous void network persist and still do not show evolution with film thickness. One would expect that increasing plasma power would mitigate against the column formation or at least promote tapered, cauliflower-type growth, if columns did persist. What actually occurs is a systematic decreasing of the void size and the persistence of the same uniform, oriented columns.

Figure 3:
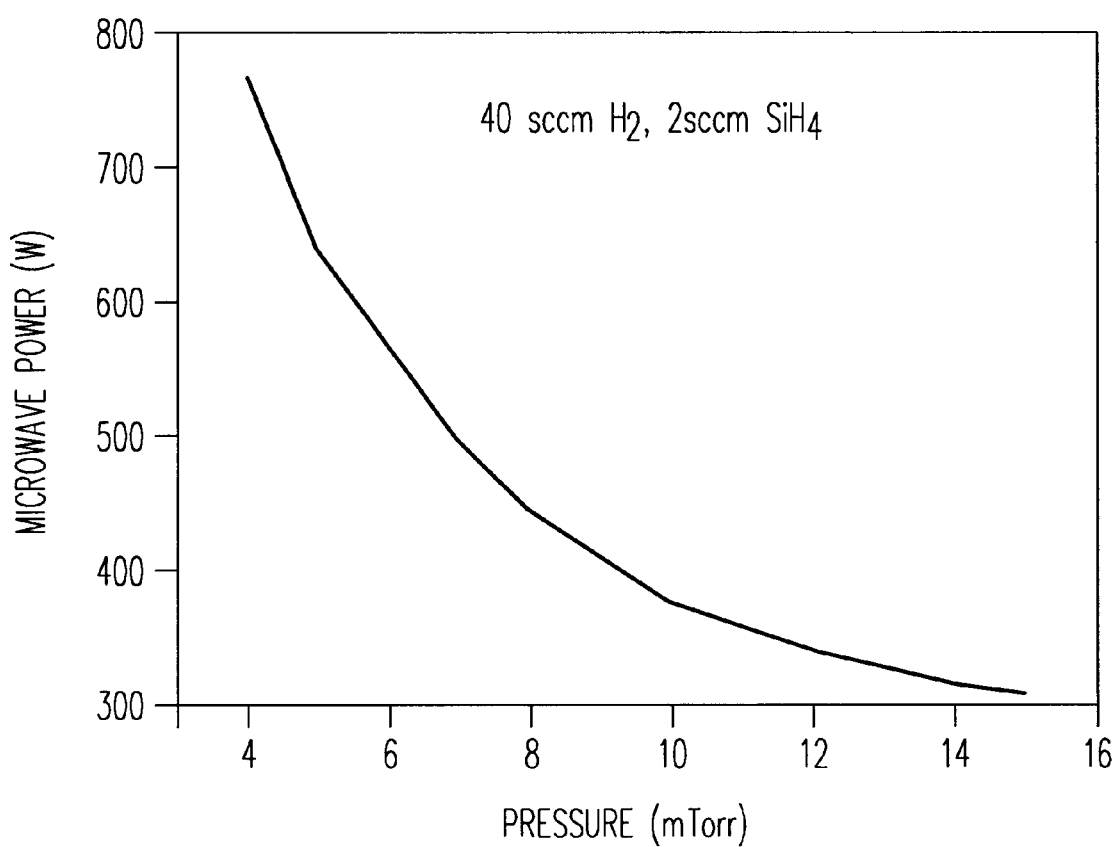
FIG. 3 is a graph exhibiting the relationship between the absorbed microwave power and the process pressure where the hydrogen and silane flow rates are 40 sccm and 2 sccm, respectively.

It was discovered that when varying plasma power in the system, the pressure is not really independent. To be specific, for a given process pressure and gas flow rate, the hydrogen plus silane ECR plasma utilized in this demonstration is only stable if the incident microwave power is above a certain threshold level. At this threshold level or just above all the incident power is absorbed by the plasma. If the power level is further increased above this threshold level, the absorbed power changes only little and the excess power is reflected. Therefore, the net absorbed microwave power and process pressure are strongly coupled. FIG. 3 shows the locus of absorbed power levels as pressure is varied for hydrogen and silane flow rates of 40 sccm and 2 sccm, respectively, for the particular high density plasma system used.

Figure 4:
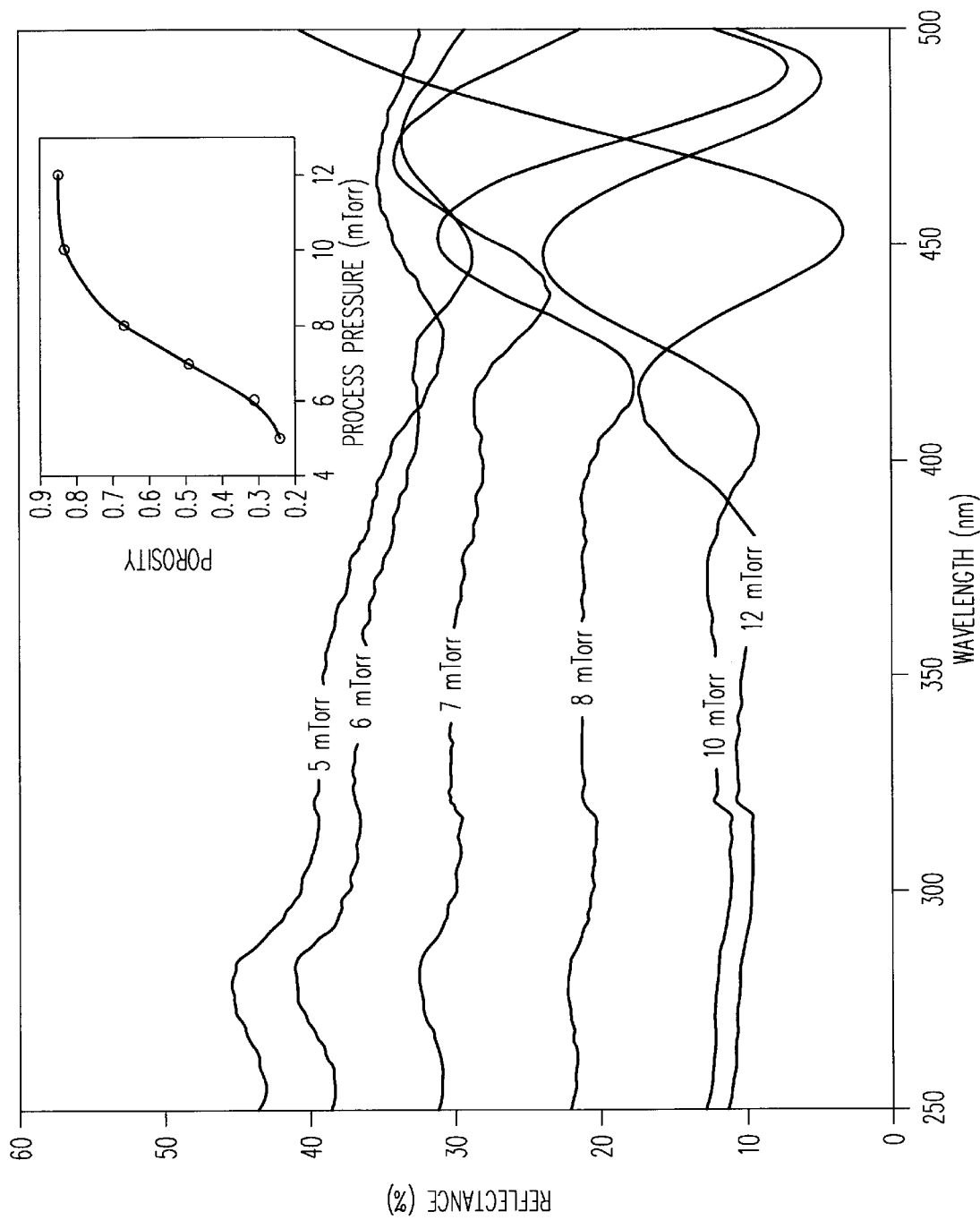
FIG. 4 is a graph monitoring reflectance with respect to a barium sulphate reflector for films deposited at 100° C. at various process pressures from 5 to 12 mTorr. The inset shows the calculated porosity.

FIG. 4 shows the optical reflectance spectra of a set of films deposited at 100° C. Again, here various process pressures correspond to certain power levels as given in FIG. 3. The peak at approximately 275 nm characterizes the films as crystalline. The spectra show interference above approximately 400 nm due to the reflected light from the substrate which is damped out towards lower wavelengths with increasing optical absorption. Therefore, based upon the dielectric mixing theory one may infer from the interference-free reflectance of the high porosity films as seen in FIG. 4 that porosity increases monotonically with the process pressure (hence with decreasing power following FIG. 3) when other deposition parameters are kept constant. The inset of FIG. 4 shows the calculated porosities based on the reflectance at 380 nm.

Figure 5A:
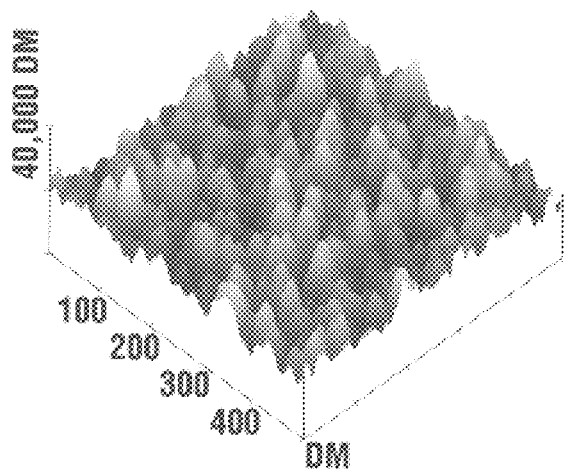
FIG. 5a is an AFM surface image of the void-columnar film deposited at 100° C. and at 6 mTorr.
Figure 5B:
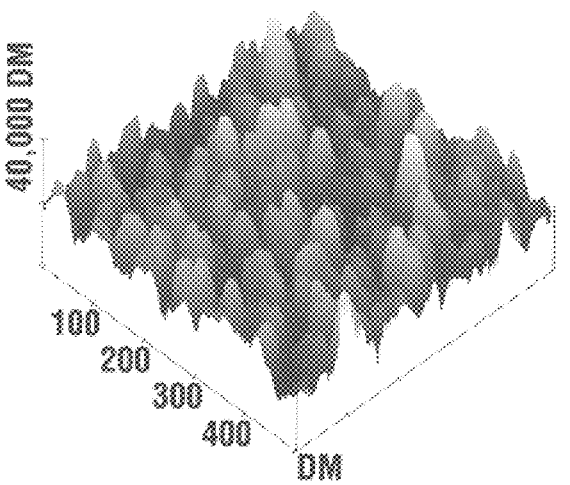
FIG. 5b is an AFM surface image of the void-columnar film deposited at 100° C. and at 8 mTorr.
Figure 5C:
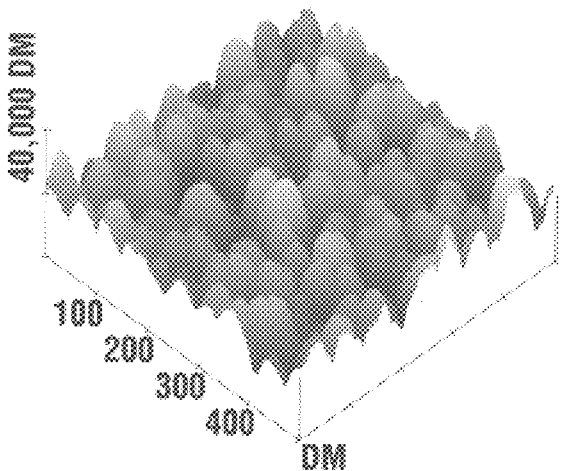
FIG. 5c is an AFM surface image of the void-columnar film deposited at 100° C. and at 10 mTorr.
Figure 6:
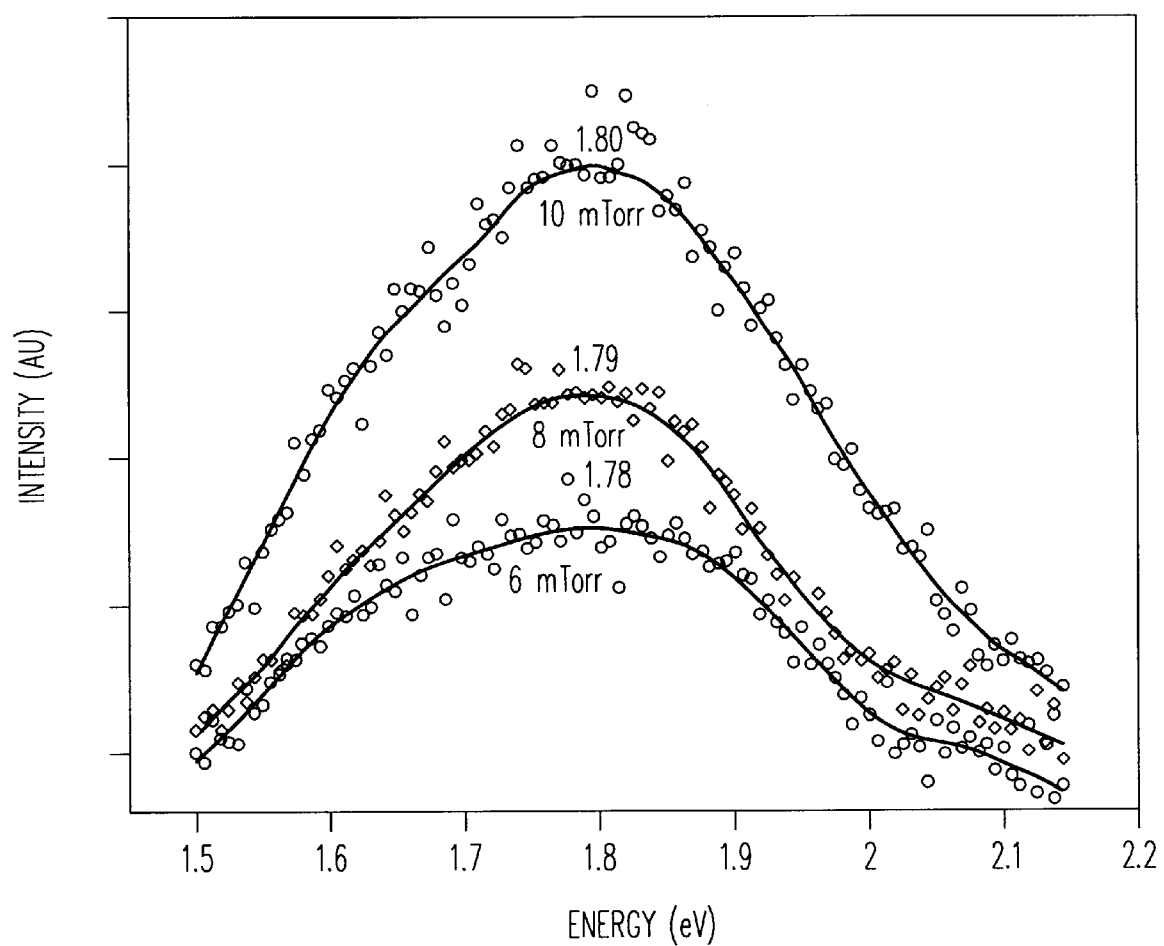
FIG. 6 is a photoluminescence spectra of the void-columnar silicon films deposited at 100° C. and at 6, 8, and 10 mTorr.

In FIG. 5, AFM surface images of the three films deposited at 100° C. and various pressures (i.e., 6, 8 and 10 mTorr) are shown. Here, the protruding features represent clusters of columns. Due to its size and shape, the AFM tip cannot trace the sudden drop in between clusters. From FIG. 5 the cluster density is seen to systematically increase with power (i.e., with decreasing pressure). As noted in FIG. 6 and discussed below, photoluminescence (PL) is seen for all these samples of FIG. 5; hence, the column size must remain in its tens of nm range for all these samples. Therefore, FIG. 5 and 6 shows decreasing pressure reduces the average porosity between clusters and columns.

As is the case for conventional electrochemically etched porous Si films, our arrayed void-column films exhibit photoluminescence. The photoluminescence spectra of the three films deposited at 100° C. and 6, 8 and 10 mTorr are given in FIG. 6. Here, the photoluminescence band peaks at ~1.8 eV with a full width at half maximum of ~0.3 eV and is similar to that observed in porous-Si. (L. Tsybeskov, MRS Bulletin, April 1998. 33 (1998)).

Magnetic Field in the Vicinity of Substrate

Figure 7:
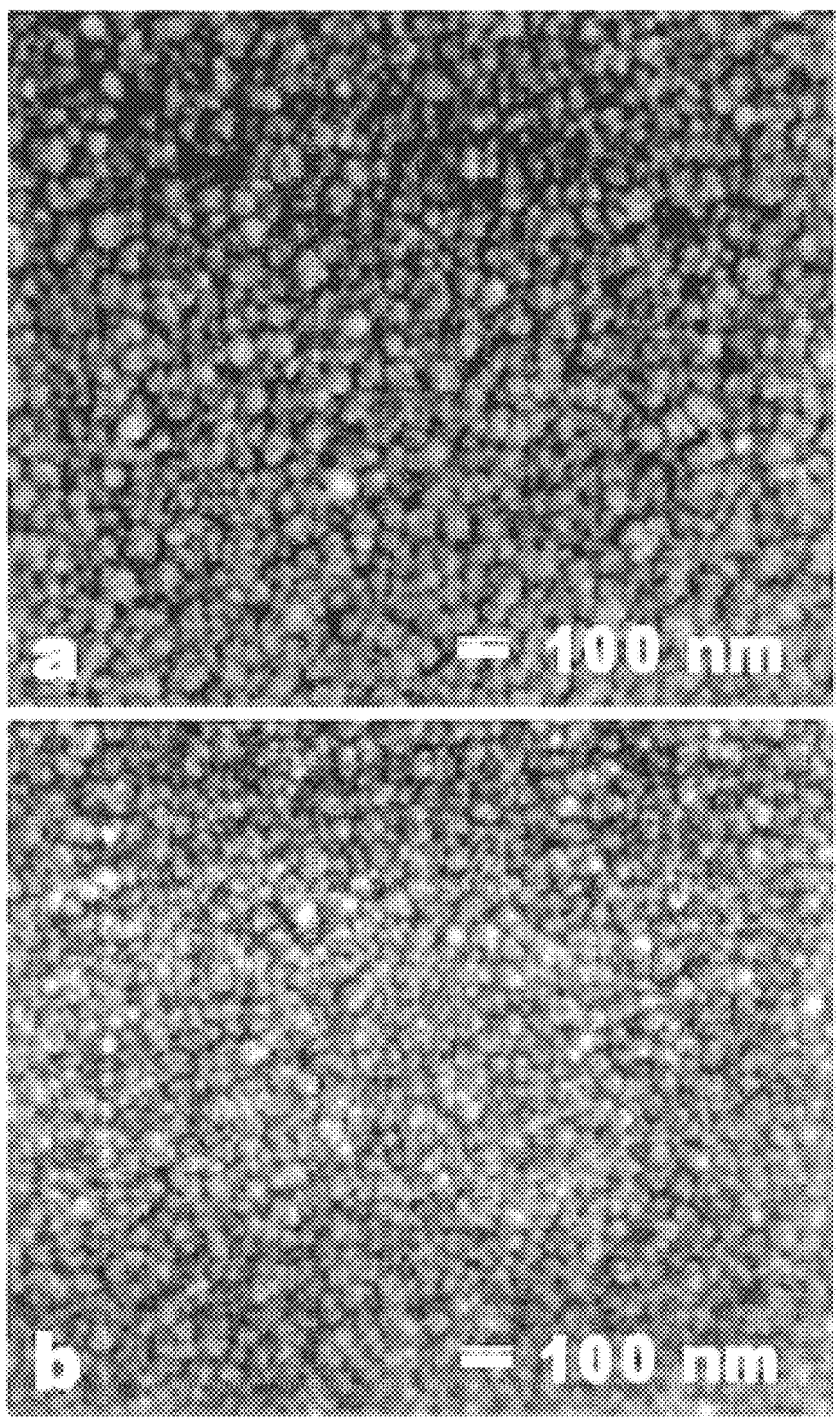
FIG. 7 shows the effect on structure caused by the magnetic field in the vicinity of the substrate. These SEM micrographs are for two films deposited at 100° C. and 10 mTorr on ITO (indium tin oxide) (a) with 100 G magnetic field normal to the substrate and (b) with no magnetic field at the substrate. The resulting calculated porosities based on reflectance data are 0.62 and 0.22, respectively.

HDP systems can have a magnetic field (MF) at or near the substrate position. This is the case in the present ECR high density plasma deposition system. It has been shown that strength of a magnetic field in the vicinity of the substrate can affect film porosity. The studies of the impact of magnetic field on film morphology indicate that controlling the magnetic field at the deposition surface may be useful in enhancing film porosity when all other deposition factors are held constant. Preferably controlling the magnetic field perpendicular to the deposition surface may be useful in enhancing film porosity. Scanning electron micrographs taken of the films as shown in FIG. 7 demonstrate that without MF at and directly above the depositing surface the structure is more densely packed; i.e., has less porosity. In fact magnetic field effects are not even considered in the structure zone model of film morphology.

Deposition Gases and Flow Rates

As can be seen from the above Table 1, a range of flow rates was explored for the precursor gases hydrogen and silane. It was found that gas composition and flow rates used to deposit the columnar films affect morphology. Of course, the gas used in the deposition must contain a silicon bearing molecule in the case of silicon, for example. However, it was found that to obtain the unique columns and continuous void (pore) structure of the films, hydrogen is also important. For example, from the literature one would expect more hydrogen radicals with increasing plasma power and, therefore, increased porosity with plasma power. However, the present inventors have discovered that porosity actually decreases with plasma power demonstrating the complex, interactions taking place. This role of hydrogen and power in deposited porous film morphology has not been observed and reported before in literature.

Hydrogen radicals probably have a role in the nucleation process that establishes the positions of the columns that will grow through the continuous void perpendicular to the transition layer. The hydrogen radical/impacting species interaction leads to an unexpected nucleation behavior compared to that discussed in the literature. To be specific, the nanostructure shown in FIG. 1 approximately corresponds to a (column forming site) nuclei density of about $6 \times 10^{11}$ cm$^{-2}$, which is much higher than encountered in nanocrystalline-silicon deposited from hydrogen diluted silane by RF-PECVD; i.e., about $3 \times 10^{10}$ cm$^{-2}$ (H. V. Nguyen and R. W. Collins, Phys. Rev. B47, 1911 (1993)). This higher nuclei density, which we show influences porosity directly and which results with a higher power, was never considered in the structural zone model normally expected to guide morphology understanding. The model proposed here is that this occurs through hydrogen radical formation effects. The column growth nuclei density may be as high as $10^{11}$ to $10^{12}$ cm$^{-2}$.

Chamber Conditioning

Chamber cleanliness affects film yield in ways that are obvious. For example, particles in the chamber are detrimental to film quality. However, the chemical state (i.e., film coating) of the chamber wall also affects films. There are fundamental chamber/plasma species interactions present due to and unique to the use of a high density plasma for deposition of these porous films. These wall/species interactions can impact the kinetics and species balance present during film growth and thereby affect porosity. For example, a silicon nitride coating on the chamber walls after each deposition is beneficial to film reproducibility and quality. $H_2$ or $O_2$ plasma chamber exposures, prior to void-column network film deposition, are other examples of conditioning. In this case these plasmas volatize ($H_2$ or $O_2$) or oxidize ($O_2$) species on the chamber walls leading to a stable, reproducible environment for a subsequent porous silicon deposition.

Substrate Surface

The state of the surface upon which the porous film is to be deposited affects the resulting film. For example, if one compares silicon wafer, indium tin oxide (ITO), bare glass, metal-coated glass, and silicon nitride-coated glass starting surfaces, porosity differences result in the deposited films. In particular, films on ITO and bare glass are very similar and yield slightly lower porosity than nitride coated glass. Hence a higher porosity correlates with a higher structure mismatch between the film and substrate, which possibly leads to a lower nuclei density.

Figure 8:
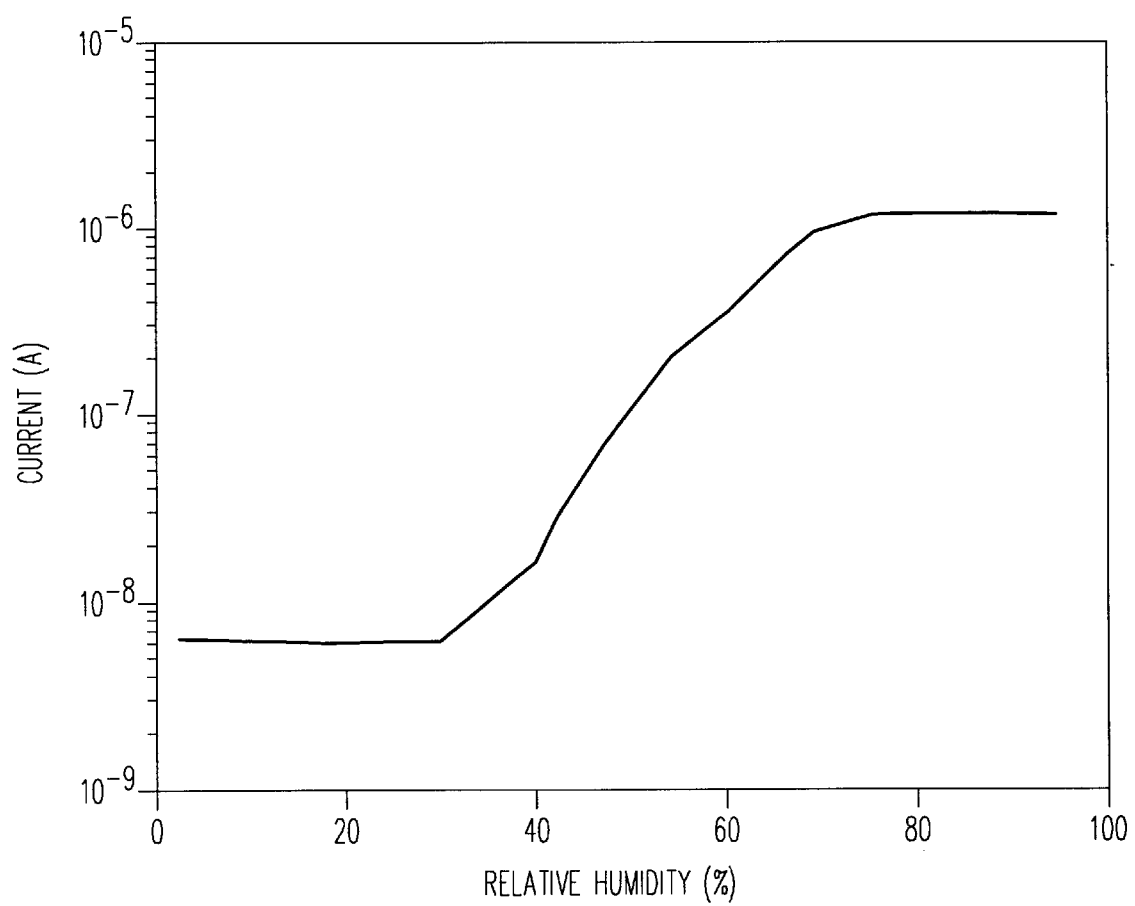
FIG. 8 is a graph representing conductivity (current passed at a fixed voltage of 10V) enhancement of a void-columnar silicon film in response to increasing relative humidity (RH). This film was deposited at a temperature of 100° C. and pressure at 8 mTorr. This film had a Pd-stabilizing treatment prior to use. The measurement was carried after a deposition of 100 Å thick Pd layer and subsequently annealing at 600° C. for 1 hour for improved reproducibility. The applied voltage is 10V.

The present films display a number of the properties heretofore only reported for wet electrochemically produced porous silicon. For example, they display the gas and vapor sensitivity reported for electrochemically etched porous silicon. (I. Schecter et al., Anal. Chem. 67, 3727 (1995)). As a preliminary investigation, the sensitivity of our films to water vapor was studied. FIG. 8 illustrates the typical behavior of the films in response to variations in RH. Depending on pore size, a weak response is found up to a threshold humidity level above which a steep (generally exponential) increase is observed. The on-set of this steep behavior is controlled by pore size and stability/sensitizing treatments. In the case of FIG. 8, a Pd layer was deposited on the deposited porous Si and annealed at 600° C. for one hour.

The enhancement in conductivity is attributed to the capillary condensation of water inside the voids. Similar behavior is observed for ceramics and the charge transport has been considered to be via protons ($H^+$), hydronium ions ($H_3O^+$), or hydroxyl ions ($OH^-$). (T. Hubert, MRS Bulletin, 49 (June 1999); B. M. Kulwicki, J. Am. Ceram. Soc. 74, 697 (1991)). Once the silicon surface interacts with humidity, the formation of chemically bonded hydroxyl ions induces a high charge density and a strong electrostatic field. Hence, additional water molecules physisorbed on this chemisorbed layer can easily dissociate into ions ($2H_2O \leftrightharpoons H_3O^+ + OH^-$) because of this high electrostatic field. (T. Hubert, MRS Bulletin, 49 (June 1999); B. M. Kulwicki, J. Am. Ceram. Soc. 74, 697 (1991)). The proton transport occurs when a $H_3O^+$ releases a proton to a neighboring $H_2O$ transforming it into $H_3O^+$, and so forth (Grotthuss chain reaction). ((T. Hubert, MRS Bulletin, 49 (June 1999); B. M. Kulwicki, J. Am. Ceram. Soc. 74, 697 (1991)). The steep rise in conductivity is possibly associated with growth of molecular layers of water with increasing RH. (J. J. Mares et al. Thin Solid Films 255, 272 (1995)). Finally, saturation follows the steep increase in conductivity with increasing RH. At this point, the complete filling of the void volume with condensed water is considered to occur. Therefore, for a given surface tension, or adsorption coefficient, the saturation is expected to occur at higher RH for larger void or pore size, as also addressed by Kelvin's relation to capillary condensation. (T. Hubert, MRS Bulletin, 49 (June 1999); J. J. Mares et al. Thin Solid Films 255, 272 (1995)).

Figure 9:
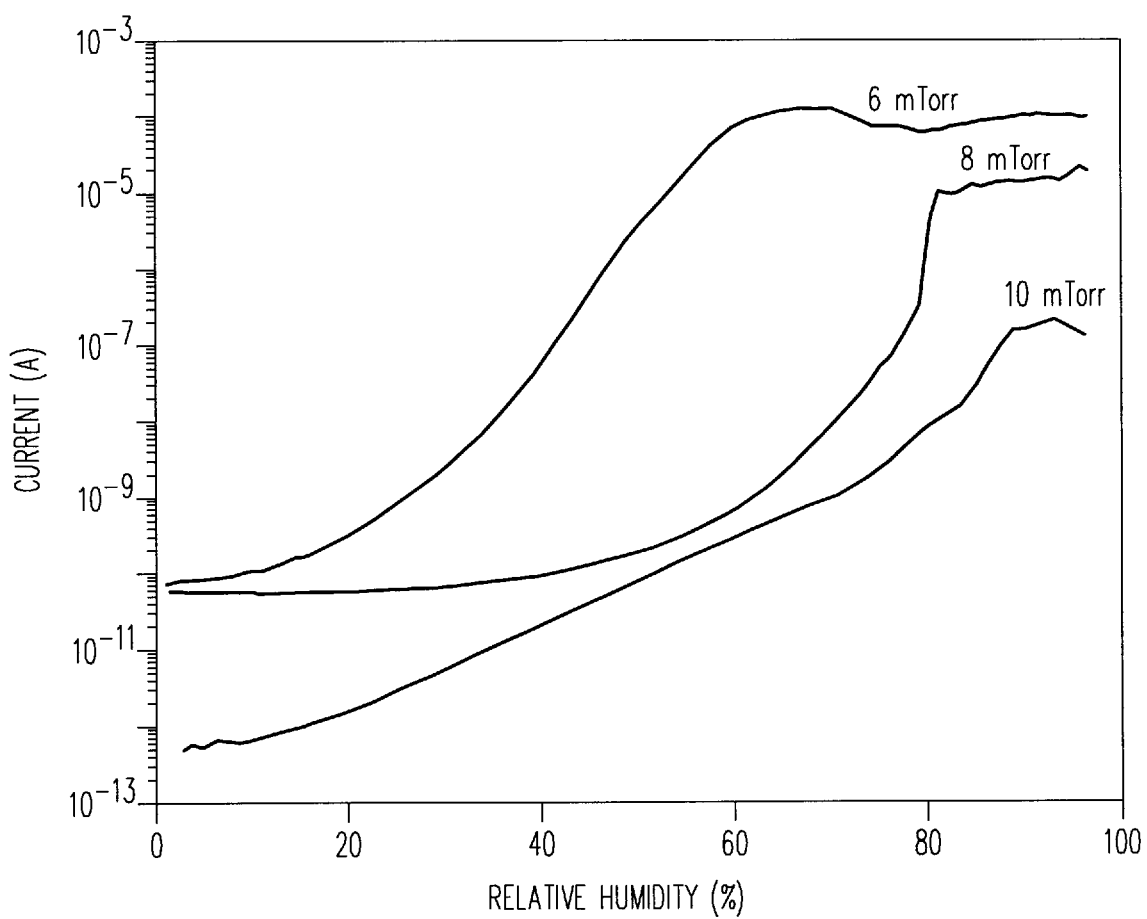
FIG. 9 is a graph representing conductivity behavior of void-columnar silicon films of different porosities in response to varying relative humidity (RH). Films were deposited at three different pressures of 6, 8, and 10 mTorr. The applied voltage is 50 V. The measurements were taken after the Lewis acid treatment. These films were given a Lewis acid exposure prior to use.
Figure 10:
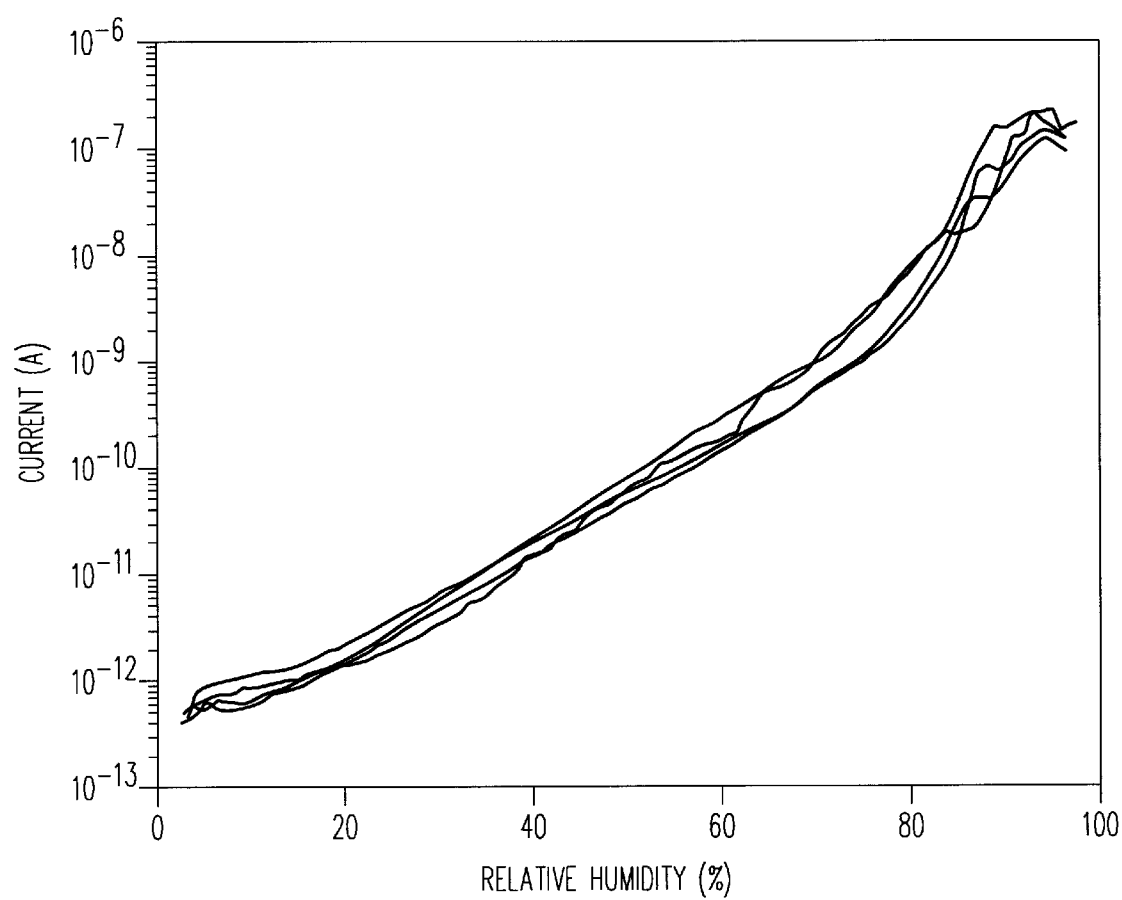
FIG. 10 is a graph of several current vs. relative humidity measurements showing repeatability and stability, taken with an applied voltage of 50 V using the void-columnar film deposited at 100° C. and 10 mTorr. This film was given a Lewis acid exposure prior to use.

FIG. 9 shows the stabilized humidity response of the three films deposited at 100° C. and various pressures (6, 8 and 10 mTorr). Among these films, the one deposited at 10 mTorr (the highest porosity film) shows the most regular behavior. FIG. 10 shows several measurements taken from this high porosity film which follow each other by minutes, hours and days. Obviously, the reproducibility is significant. The data of FIGS. 8–10 are for films given stabilization / sensitization treatments. Such treatments need not be used.

Mares et al. have reported a similar conductivity enhancement (of three orders of magnitude) from electrochemically prepared porous Si upon variation of RH from 0 to 100% yielding the similar S-shaped curve as in FIG. 8. (J. J. Mares et al., Thin Solid Films. 255, 272 (1995). However, their measurements involved a high level of instability taking days for stable readings. This is because, with the presence of the inherent silicon material underlying the electrochemically prepared porous silicon layer, the electric current can only be transported across the thickness of the porous silicon layer. If a lateral electric field were used for these electrochemically prepared samples, it would cause the current to shunt through the silicon wafer rendering the lateral monitoring of the electrical properties impossible. Hence, a sandwich monitoring structure with the conventional porous silicon located between two electrodes is required. This is a major disadvantage as the water vapor has to pass through the top electrode (contact) before reaching the porous semiconductor layer. As a result, the sensitivity as well as the response time is strongly degraded.

On the other hand, once the porous films are on an insulator, as is easily accomplished with the deposited void-column network material, the electrical properties can easily be monitored laterally with a lateral contact configuration. This structure allows direct interaction between the ambient and the monitored film in the area between the contacts. As a result, the films exhibit response times within fractions of a second when RH is changed suddenly from 0 to 100% or vice versa. Furthermore, in the present morphology the voids are interconnected even for lower porosities resulting in a continuous void network aligned normal to the film/ambient interface throughout the film. This facilitates a uniform and rapid mass transfer in and out of the films. Electrochemically prepared porous silicon films lack this feature as the voids are not necessarily interconnected.

In FIG. 9 the shift of the RH where saturation occurs is indicative of different void sizes for the three films. According to the discussion about capillary condensation above, an increasing void size is inferred with increasing process pressure (decreasing power). This is in full agreement with our conclusions from the AFM and PL data. Therefore, this work confirms that behavior of conductance of porous films with RH provides valuable information about the morphology. Because of its highest porosity and thickness, the 10 mTorr sample is expected to yield the highest current when all void volume is filled with condensed water. However, what actually occurs is just the opposite in that the saturation current decreases with the void volume (being proportional to porosity times film thickness) as seen from FIG. 9 (from 6 mTorr to 10 mTorr). This is probably because, for the present films, the dominant charge transport does not take place in the bulk liquid, but near the silicon surface where water most effectively dissociates due to the surface charge. The ionization fraction at the surface is estimated to be only 1%, but this is six orders of magnitude larger than that in liquid water. (B. M. Kulwicki, J. Am. Ceram. Soc. 74, 697 (1991)). Accordingly, the 6-mTorr sample, which accommodates the highest density of columns, shows the highest saturation current due to its highest inner surface area. On the other hand, the 10 mTorr film does not only possess the lowest inner surface area, but also the largest average separation. The longer the separation, the more the ion concentration will fall towards the middle of the separation from its value at the surface and hence adding more series resistance.

Figure 11:
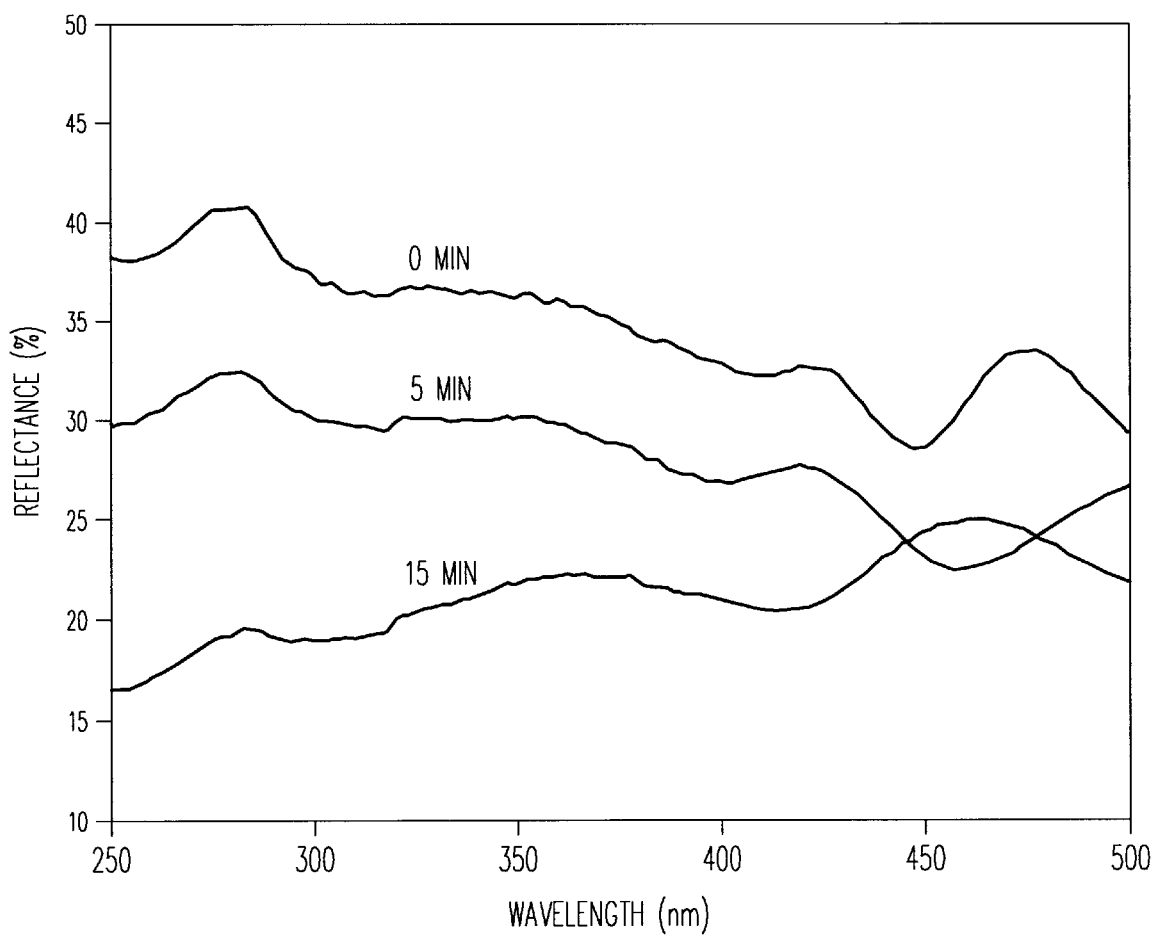
FIG. 11 is a graph of porosity enhancement of void-columnar silicon film by post deposition hydrogen plasma exposure of 5 and 15 minutes, respectively, as seen from the reflectance spectra.

Post deposition processing in situ or ex situ can be used to tailor morphology, sensitivity, and specificity. For example, FIG. 11 shows the enhancement of porosity by post-deposition-etching hydrogen plasma etching. This porosity enhancement with plasma exposure time is attributed to reduction of the diameters of the silicon columns, clusters or both. As mentioned above the films may be modified after deposition by exposures at elevated temperatures, chemical interactions, subsequent deposition, wet exposures, and/or certain plasma exposures. As a further example, F-terminated or Cl-terminated surfaces in the porous films can be attained to avoid degradation. The film surface can be functionalized with chemical, biological, or plasma treatments to make it more sensitive to specific detection targets other than water vapor.

Figure 12A:
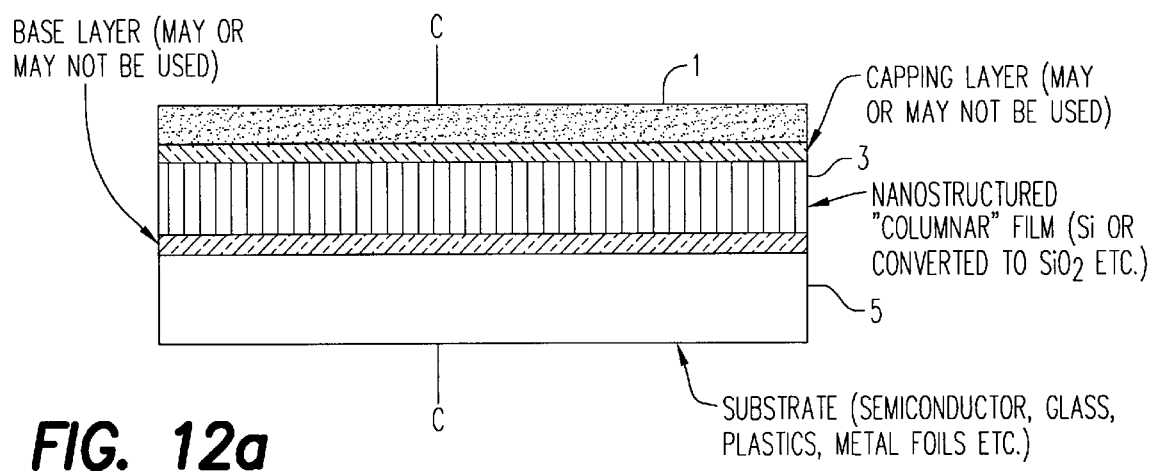
FIG. 12a shows a basic configuration useful for creating isolation or confinement regions defined by removal of porous material. Included in this basic configuration are a capping layer, nanostructured "columnar" film, base layer and substrate.
Figure 13:
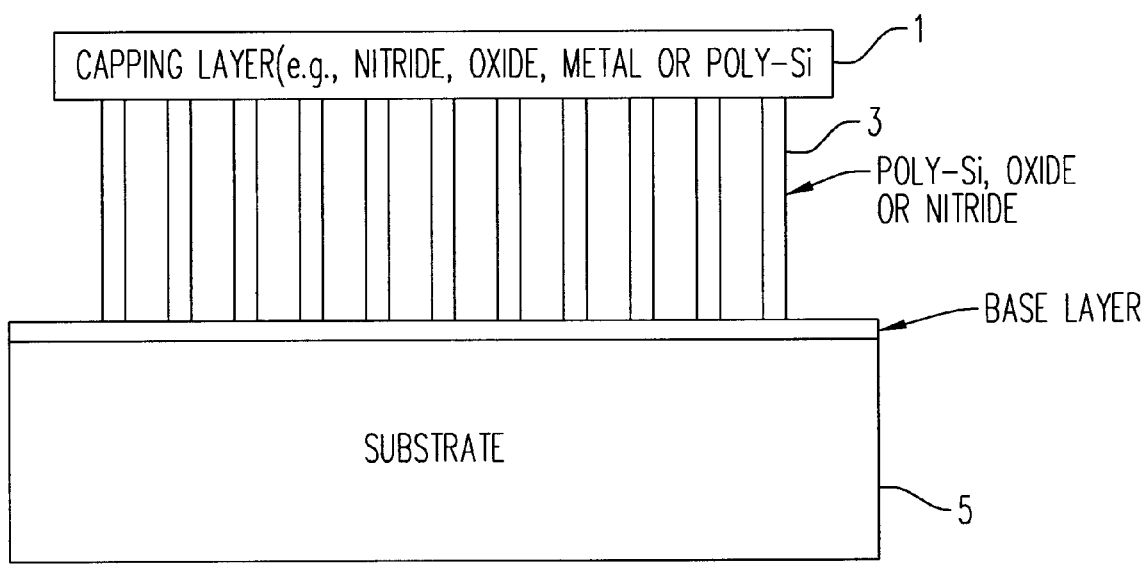
FIG. 13 shows several layers of a basic configuration useful for creating isolation or confinement regions using porous material. Shown are two porous layers, a capping layer, base layer and substrate.

These porous void-column network silicon films, with their controlled porosity, that are disclosed here can also be used for a variety of isolation, separation layers, void formation, and confinement applications due to their ability to be quickly, reproducibly, and controllably etched. They can be used for chemical, electrical, physical, and mechanical isolation. We refer to all types of such applications as "airgap", isolation, or "release layer" uses. In the case of electrical isolation, for example, these films can be oxidized to produce columns of $SiO_2$ in a two dimensional array (layer 3 of FIG. 12a). The resulting air/$SiO_2$ material will have a very low dielectric constant, as is needed where capacitive coupling must be minimized. One specific application is in interconnects in microelectronics. A capping layer can then be deposited on this two-dimensional array as seen in FIG. 13 which shows two 2-D array layers (layer 3). Electrical connections can then be in layer 1, the base layer, and/or the substrate. Interconnections among these layers can be accomplished by doping or other conducting conduits through the porous layers.

Such electrical connections or circuits would have minimal electrical capacitive coupling to conductors or circuits in or on the substrate or other layers due to the excellent electrical isolation properties of the two-dimensional (2-D)

air/SiO$_2$ array; i.e. due to the low dielectric constant of the porous isolation layer. For example, when a silicon oxide bridge structure contains 70% porosity, the effective dielectric constant of the structure can be 1.84.

Figure 12B:
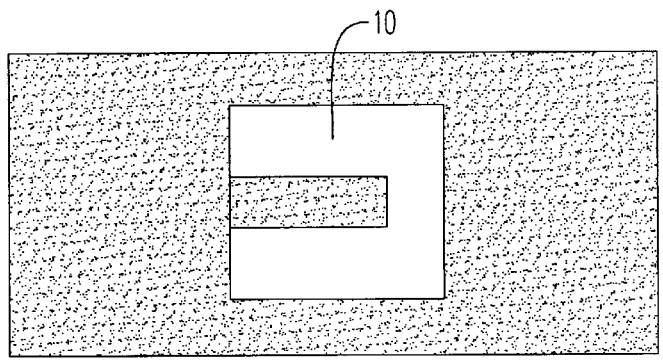
Figure 12C:
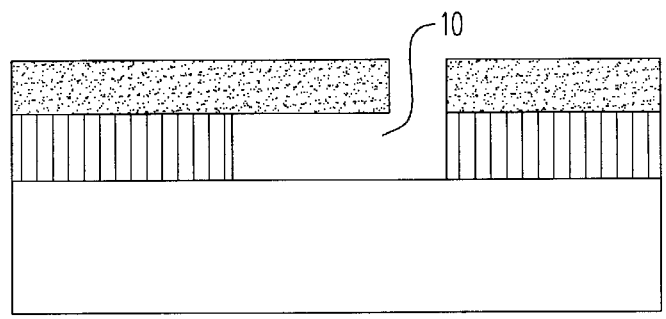
Figure 14:
FIG. 14 shows a tube or "airgap" created by removal of void-column network deposited porous silicon.

Mechanical, physical, and chemical isolation can also be achieved with the unique deposited, controlled structured film presented by the void-column network by removal of this material in selected regions. For example, a capping layer 1 can be deposited directly on the film 3 which can remain silicon or be chemically reacted to SiO$_2$, a metal silicide, or other silicon compound. Capping layers can be formed with or without breaking vacuum and, as seen in FIG. 12, a nitride, oxide, metal, or another non-porous, (i.e. continuous) silicon layer or cap 1 can be deposited to cap the 2-D void-column network or film 3 which is disposed on substrate 5 (e.g., semiconductor, glass or plastic). As seen in FIGS. 12(*b*) and 12 (*c*), conventional approaches such as lithography can then be used prior to the capping deposition or after the capping deposition to define etching access holes 10. These holes 10 allow etchants to enter the porous void-column network silicon (or SiO$_2$, etc.) and to remove it in predetermined regions as seen in FIG. 12(*b*). As a result, isolation or confinement regions are defined by removal of the porous material. The porous silicon void-column network material is easily removed by this etching since every region of the porous material silicon is accessible due to the continuous network of voids or pores which allows enchant access and reaction product removal. FIG. 14 shows an actual "airgap" structure fabricated by the removal of such a void-column network Si region. Here the processing is seen to have created a cavity between insulator layers. In this particular demonstration, the cavity was etched out in twenty minutes. Prior art approaches, using polycrystalline silicon to create the cavity, can take an order of magnitude more time or use complicated e-beam lithography to try to enhance etching (P. J. French, J. Micromech. Microeng., 6, 197 (1996)).

The removed regions (cavities or "airgaps") such as that demonstrated in FIG. 14 can be used as tubes for applications such as chromatography, DNA sorting, optical applications, and fluidics as well as in diaphragms, accelerometers, bolometers, and reduced capacitive coupling.

Figure 15:
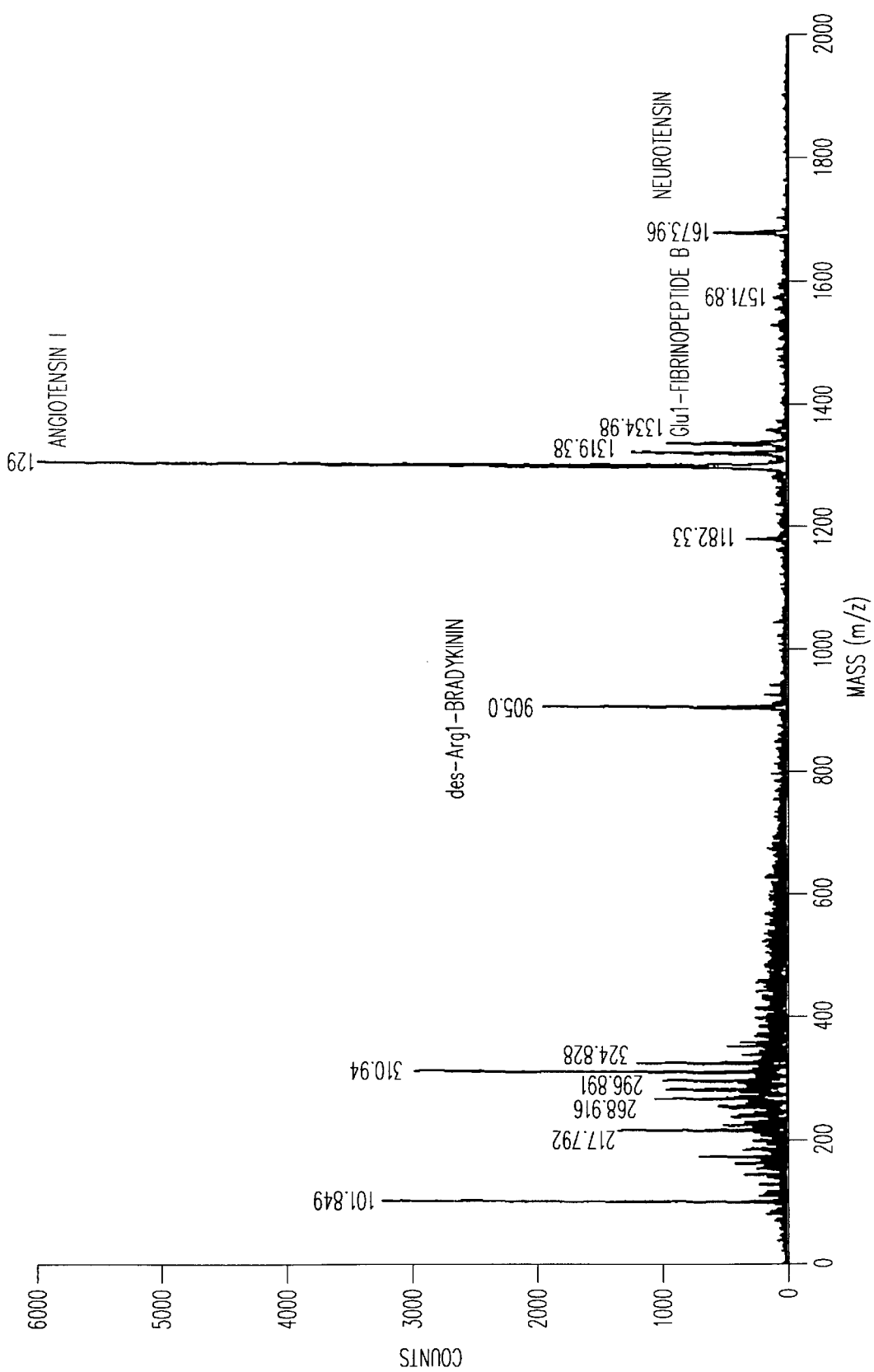
FIG. 15 is a laser desorption spectrum in which sample drops were applied directly to a porous silicon film and allowed to dry prior to laser impingement. Identification of molecules in the sample is seen.

FIG. 15 shows the use of the deposited porous films in another demonstrated application: support substrates for mass desorption spectroscopy. Here the deposited porous silicon is serving as a medium for the attachment of molecules for subsequent detection. Detection occurs by using a laser to desorb the molecules from the adsorbing porous silicon and to cause ionization. The ions resulting from these desorbed molecules are then identified using mass spectroscopy. The identification of several molecules that had been purposefully adsorbed on a deposited porous silicon film is seen in the mass spectroscopy scan of FIG. 15. Using a laser to desorb molecules from a substrate and subsequent mass spectroscopy has been accomplished previously but it required an organic "matrix" to bind the molecules to be detected. This is the so-called mass analysis by laser desorption and ionization (MALDI) technique. Our technique avoids the use of the organic matrix binder material. As can be seen, laser exposure results in desorption and ionization leading to identification of molecules. Electrochemically etched porous silicon substrates have also been shown to be effective in a limited mass range for this laser-desorption induced spectroscopy. They too avoid the use of a binder (Nature, vol. 399, p.243–246, (1999)). However, this etched porous silicon approach has the problems we have noted earlier: it requires electrochemical etching, back electrical contacts, and thick starting silicon to achieve the nanostructure needed to the bind molecules to be detected. Our films have a deposited nanostructure, require no etching step, and can be deposited on any substrate including plastics.

In all these and other applications, the approach to producing deposited porous silicon presented here yields some distinct advantages over the electrochemical wet etch materials and over previous deposited materials. These advantages fall into four major groups: (1) variability of substrate, (2) adjustability of porosity and film phase, even for thin films. (3) consistency of porosity with thickness, and (4) flexibility of plasma-based processing.

With the low temperature direct deposition approach of this invention porous semiconductor films can now be obtained on any substrate including insulators, metal foils, and plastics. The present films can be doped or undoped and can be any thickness greater than about 10 nm thick, preferably between 10 to 20 nm. The electrochemical approach requires the porous semiconductor layers be obtained on conductive substrates or layers, only. The starting material must be doped and of sufficient thickness to insure the etched material attains the required morphology. The previous deposition approaches yield a morphology that also varies with film thickness, could achieve the degree of porosity of our films only after a separate etch step, and always resulted in an amorphous phase material. With plasma based processing and the parameters and conditioning we employ, simultaneous etching and deposition yields a dry process with controlled porosity and phase for thin films deposited on any substrate.

As noted, the fact that these films can be deposited on insulating structures facilitates their use in sensor structures. Furthermore, the distinct nanostructure of the present invention with a continuous and uniform void network and void volume aligned perpendicular to the film surface facilitates the mass transfer into and out of the films in applications such as electrical sensors, electrophoresis and chromotography as well as mass-desorption applications. This feature of aligned, void-column network morphology with untapered columns and relatively uniform and continuous voids is found only in the present porous silicon. It renders the present films particularly superior for adsorption, desorption, transport, and immobilization applications (e.g., immobilizing and fixing species such as DNA for identification and sorting and fixing as well as contacting molecules for molecular electronics, etc). With the direct deposition approach, porous semiconductors can also be obtained on any sort of optical material substrate: transparent, polarizable, etc. This facilitates and broadens the use of porous semiconductors in optical applications such as antireflection, optical cavity, and light trapping coatings. Finally, once porous semiconductors are deposited on flexible polymeric substrates, nonplanar, curved porous semiconductor layers can also be made available.

This approach exploits the advantages of plasma-based processing technology. For example, the chemical composition of the present high porosity silicon films can be controlled by the precursor gases being incorporated into the plasma during the simultaneous deposition-etching process. This enables producing not only intrinsic, n-type or p-type porous-Si but also porous Ge, Ge:C, Si:C, Si:O, Si:F, Si:Cl, etc. Furthermore, the film's chemical composition can be varied during deposition and, therefore, throughout the film thickness. In contrast, by electrochemical etching of a previously grown material the chemical composition of the porous-silicon layer cannot be determined anywhere other than at the eventual surface, and the control of that surface composition is limited by the electrolyte used. Because the films of this invention are grown under high vacuum, contamination due to air exposure can be prevented, while conventional porous silicon films can be easily contaminated because they are processed in wet chemicals.

Whether one is using the standard electrochemical etching or the present plasma deposition approach, the resulting porous silicon material will be terminated by hydrogen atoms at the immediate completion of preparation. However, in ambient conditions, this hydrogen-terminated surface shows substantial susceptibility to room-temperature oxidation and hydrogen loss. Both of these mechanisms can lead to degradation of the physical properties of porous silicon. Therefore, degradation of porous silicon films can be avoided if a stable surface passivation is achieved immediately. This is attained with the vacuum-based processing by using a multichamber system and implementing coating, dipping, vapor exposures, etc. in a separate chamber or by switching chamber ambients in situ after film deposition-etching. In this respect, the present high density plasma approach is very flexible as it promotes any kind of reactions at lower activation energies, making plasma-based surface treatments easily achievable. In general, the chemistry of the surface may be controlled during or after deposition. As an example, F-terminated or Cl-terminated surfaces in the porous films can be attained in situ and such surfaces are believed to be more resistant to degradation. Of course, the porous films can be treated ex-situ and rendered hydrophobic or hydrophilic with surface treatments. The present films can be functionalized with surface treatments.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A nano-scale composition comprising:
   a) a plurality of polycrystalline or amorphous rod-like structure units penetrating a continuous void, and
   b) a substrate to which said plurality of rod-like structure units are uniformly orientated and adhered.

2. A composition according to claim 1 wherein said composition is deposited.

3. A composition according to claim 2 wherein said composition is formed by means comprising vapor deposition.

4. A composition according to claim 3 wherein said deposited composition is formed by means comprising use of a high-density plasma.

5. A composition according to claim 2 wherein said means of deposition controls the spacing, height, and/or diameter of said basic structure units.

6. A composition according to claim 2 wherein said continuous void comprises up to 90% of its volume.

7. A composition according to claim 2 wherein said basic structure units have a diameter from 1 to 100 nm.

8. A composition according to claim 2 wherein said composition has a thickness greater than 10 nm.

9. A composition according to claim 2 wherein said basic structure units are agglomerated in adjustably sized columnar-like clusters penetrating a continuous void and adhering to said substrate.

10. A composition according to claim 2 wherein said basic structure units are comprised of silicon, germanium, carbon, hydrogen, other inorganics, or mixture thereof.

11. A composition according to claim 2 wherein said substrate comprises semiconductors, glasses, plastics, polymers, metals, ceramics, insulators, or mixtures thereof.

12. A composition according to claim 11 wherein said substrate is a semiconductor.

13. A composition according to claim 11 wherein said substrate is glass.

14. A composition according to claim 11 wherein said substrate is plastic.

15. A composition according to claim 11 wherein said substrate is a metal.

16. A composition according to claim 2 wherein said continuous void contains solid or liquid material, atoms, molecules, or mixtures thereof.

17. A composition according to claim 16 wherein said void contains organic or inorganic material or mixtures thereof.

18. A composition according to claim 17 wherein material or mixture thereof is selected from the group of molecules, polymers, electrolytes, solutions, metals, metal alloys, semiconductors, doped insulators, dielectrics, and carbon forms.

19. A composition according to claim 2 wherein said continuous void is capable of adsorbing solid or liquid material, atoms, molecules, or mixtures thereof.

20. A composition according to claim 19 wherein said void is capable of adsorbing organic or inorganic material or mixtures thereof.

21. A composition according to claim 19 wherein material or mixture thereof is selected from the group of molecules, polymers, electrolytes, solutions, metals, metal alloys, semiconductors, doped insulators, dielectrics, and carbon forms.

22. A composition according to claim 18 wherein said composition has photovoltaic properties.

23. A composition according to claim 18 wherein said composition has light emission properties.

24. A composition according to claim 18 wherein said composition has controllable light transmitting properties.

25. A composition according to claim 18 wherein said composition has tailorable chemical properties.

26. A composition according to claim 21 wherein said composition has photovoltaic properties.

27. A composition according to claim 21 wherein said composition has light emission properties.

28. A composition according to claim 21 wherein said composition has controllable light transmitting properties.

29. A composition according to claim 21 wherein said composition has tailorable chemical properties.

30. A composition according to claim 2 for use in a device selected from the group consisting of: microfluidic devices; fuel cells; sorting structures; gas/vapor sensors; mass spectroscopy/laser desorption; micro-electro-mechanical devices; thermal/dielelectric isolation; analytical devices; airgap devices; separation layers; sacrificial layers, chemical delivery, chromatography, or combinations thereof.

31. A composite structure which comprises:
   a substrate; and
   a porous film comprising a plurality of polycrystalline or amorphous rod-like units extending therefrom into a void having a porosity of up to 90%.

32. The composite structure of claim 31, further comprising a substrate coating layer such that said porous film is disposed on said substrate coating layer.

33. The composite structure of claim 32, wherein said substrate coating layer is at least one coating material selected from the group consisting of: insulators, nitrides, and oxides.

34. The composite structure of claim 32, wherein said coating layer is at least one active material selected from the group consisting of: piezoelectrics, ferroelectrics, metals, and semiconductors.

35. The composite structure of claim 31, further comprising a capping layer, such that said porous film is disposed between said capping layer and said substrate.

36. The composite structure of claim 35, wherein said capping layer is at least one insulation material selected from the group consisting of: insulators, nitrides, and oxides.

37. The composite structure of claim 35, wherein said capping layer is at least one active material selected from the group consisting of: piezoelectrics, ferroelectrics, metals, and semiconductors.

38. The composite structure of claim 35, wherein said porous film has a thickness greater than about 10 nm.

39. The composite structure of claim 31 wherein said rodlike perturbations have a diameter of between about 1 to 50 nm.

40. The composite structure of claim 39, wherein said rodlike perturbations are found in clusters with a diameter between about 50 to 500nm.

41. The composite structure of claim 31, wherein said substrate is selected from the group consisting of: glass, metal foil, insulation material, plastic material, and semiconductor-containing material.

42. A sensor which comprises a composite structure having:

a substrate; and a porous film comprising a plurality of polycrystalline or amorphous rod-like units extending therefrom into a void having a porosity of up to 90%.

43. The sensor of claim 42, wherein said sensor is capable of monitoring lateral resistivity, optical, or dielectric response.

44. A gas detector which comprises a composite structure having:

a substrate; and a porous film comprising a plurality of polycrystalline or amorphous rod-like units extending therefrom into a void having a porosity of up to 90%.

45. An analytical device which comprises a composite structure having:

a substrate; and a porous film comprising a plurality of polycrystalline or amorphous rod-like units extending therefrom into a void having a porosity of up to 90%.

46. The analytical device of claim 45, wherein said device is capable of desorption mass spectroscopy.

47. A composition according to claim 1 wherein each said unit has a diameter that is essentially uniform with height.

48. A composition according to claim 1, wherein said units have regular spacing and uniform height.

49. A composition according to claim 1, wherein said structure units have a diameter between 1 and 50 nm.

50. A composition according to claim 1, wherein said structure units are in a two-dimensional periodic array.

51. A composition according to claim 1 wherein said composition is formed by means comprising use of a highly reactive or dense plasma system.

52. A composition according to claim 4, wherein said high density plasma is selected from the group consisting of: electron cyclotron resonance plasma enhanced chemical vapor deposition; helicon plasma; helical resonator; inductively coupled plasma; transformer coupled plasma; electron beam plasma; and any combinations thereof.

53. The composite structure according to claim 31, wherein said film is disposed on said substrate by deposition at a temperature of less than 250° C.

* * * * *